US008038682B2

(12) United States Patent
McGill et al.

(10) Patent No.: US 8,038,682 B2
(45) Date of Patent: Oct. 18, 2011

(54) APPARATUS AND METHODS FOR DELIVERING COMPOUNDS INTO VERTEBRAE FOR VERTEBROPLASTY

(75) Inventors: Scott McGill, San Ramon, CA (US); Harold F. Carrison, Pleasanton, CA (US); Mukund R. Patel, San Jose, CA (US); Shana Castelli, San Francisco, CA (US); Austin Hendricks, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1655 days.

(21) Appl. No.: 10/920,581

(22) Filed: Aug. 17, 2004

(65) Prior Publication Data
US 2006/0052794 A1 Mar. 9, 2006

(51) Int. Cl.
*A61B 17/58* (2006.01)
(52) U.S. Cl. .......................................... 606/94
(58) Field of Classification Search ............... 606/92–94
See application file for complete search history.

(56) References Cited

U.S. PATENT DOCUMENTS

| | | |
|---|---|---|
| 1,458,282 A | 6/1923 | Fairbanks |
| 1,612,996 A | 1/1927 | Waagbo |
| 1,954,143 A | 5/1933 | Morrison |
| 1,998,692 A | 4/1935 | Van Rossem et al. |
| 2,338,428 A | 1/1944 | Guter et al. |
| 2,745,575 A | 5/1956 | Spencer |
| 2,818,999 A | 1/1958 | Miller |
| 2,825,134 A | 3/1958 | Hicks |
| 2,874,877 A | 2/1959 | Spencer |
| 3,140,078 A | 7/1964 | Krahe et al. |
| 3,164,303 A | 1/1965 | Trautmann |
| 3,188,057 A | 6/1965 | Trumbull |
| 3,195,778 A | 7/1965 | Coates |
| 3,216,616 A | 11/1965 | Blankenship, Jr |
| 3,475,010 A | 10/1969 | Cook et al. |
| 3,581,399 A | 6/1971 | Dragan |

(Continued)

FOREIGN PATENT DOCUMENTS

EP   1 400 213 A1   7/2003

(Continued)

OTHER PUBLICATIONS

Partial PCT International Search Report for PCT/US2005/028925, Applicant Boston Scientific Scimed, Inc., Forms PCT/ISA/216, dated Apr. 20, 2005 (6 pages).

(Continued)

*Primary Examiner* — Thomas C. Barrett
*Assistant Examiner* — Michael Araj
(74) *Attorney, Agent, or Firm* — Vista IP Law Group LLP

(57) ABSTRACT

An apparatus for delivering bone cement into a vertebra includes a cannula and a mix and delivery device pivotally coupled to the cannula. The mix and deliver provides a single device in which a flowable compound may be mixed and the dispensed into the vertebrae through the cannula. The mix and delivery device includes a piston, slidably disposed within a barrel of the device, for advancing the bone cement through an outlet communicating with the cannula. An actuating device, which exerts a pressure, is connected to an inlet on the mix and delivery device (either directly or through a tube). The pressure created by the actuating device is used to advance the piston within the mix and delivery device.

21 Claims, 7 Drawing Sheets

U.S. PATENT DOCUMENTS

| | | | |
|---|---|---|---|
| 3,724,077 A | 4/1973 | Preston et al. | |
| 3,752,364 A | 8/1973 | Vries | |
| 3,768,472 A | 10/1973 | Hodosh et al. | |
| 3,858,853 A | 1/1975 | Rausch et al. | |
| 4,274,163 A | 6/1981 | Malcom et al. | |
| 4,277,184 A | 7/1981 | Solomon | |
| 4,371,094 A | 2/1983 | Hutter, III | |
| 4,376,498 A | 3/1983 | Davis | |
| 4,469,153 A | 9/1984 | Morrisette | |
| 4,488,549 A * | 12/1984 | Lee et al. | 606/94 |
| 4,671,263 A | 6/1987 | Draenert | |
| 4,676,655 A | 6/1987 | Handler | |
| 4,758,096 A | 7/1988 | Gunnarsson et al. | |
| 4,799,801 A | 1/1989 | Bruning | |
| 4,889,432 A | 12/1989 | Patterson | |
| 4,944,065 A | 7/1990 | Svanberg et al. | |
| 4,952,065 A | 8/1990 | Kreuziger | |
| 4,966,468 A | 10/1990 | Bruning | |
| 4,966,601 A | 10/1990 | Draenert | |
| 4,969,888 A | 11/1990 | Scholten et al. | |
| 4,983,164 A | 1/1991 | Hook et al. | |
| 5,071,040 A | 12/1991 | Laptewicz | |
| 5,108,404 A | 4/1992 | Scholten et al. | |
| 5,143,211 A | 9/1992 | Miczka et al. | |
| 5,193,907 A | 3/1993 | Faccioli et al. | |
| 5,219,897 A | 6/1993 | Murray | |
| 5,252,301 A | 10/1993 | Nilson et al. | |
| 5,261,883 A | 11/1993 | Hood et al. | |
| 5,273,190 A | 12/1993 | Lund | |
| 5,395,167 A | 3/1995 | Murray | |
| 5,398,483 A | 3/1995 | Smith et al. | |
| 5,415,474 A | 5/1995 | Nelson et al. | |
| 5,431,654 A | 7/1995 | Nic | |
| 5,435,645 A | 7/1995 | Faccioli et al. | |
| 5,443,182 A | 8/1995 | Tanaka et al. | |
| 5,468,245 A | 11/1995 | Vargas, III | |
| 5,478,342 A | 12/1995 | Kohrs | |
| 5,514,135 A | 5/1996 | Earle | |
| 5,531,519 A | 7/1996 | Earle | |
| 5,545,460 A | 8/1996 | Tanaka et al. | |
| 5,549,381 A | 8/1996 | Hays et al. | |
| 5,588,136 A | 12/1996 | Watanabe | |
| 5,588,745 A | 12/1996 | Tanaka et al. | |
| 5,624,184 A | 4/1997 | Chan | |
| 5,676,666 A | 10/1997 | Oxland et al. | |
| 5,681,317 A | 10/1997 | Caldarise | |
| 5,718,707 A | 2/1998 | Mikhail | |
| 5,797,678 A | 8/1998 | Murray | |
| 5,797,679 A | 8/1998 | Grulke et al. | |
| 5,824,087 A | 10/1998 | Aspden et al. | |
| 5,827,289 A | 10/1998 | Reiley et al. | |
| 5,842,785 A | 12/1998 | Brown et al. | |
| 5,842,786 A | 12/1998 | Solomon | |
| 5,865,847 A | 2/1999 | Kohrs et al. | |
| 5,876,116 A | 3/1999 | Barker et al. | |
| 5,897,593 A | 4/1999 | Kohrs et al. | |
| 5,925,051 A | 7/1999 | Mikhail | |
| 5,951,160 A | 9/1999 | Ronk | |
| 5,954,728 A | 9/1999 | Heller et al. | |
| 5,961,211 A | 10/1999 | Barker et al. | |
| 5,972,015 A | 10/1999 | Scribner et al. | |
| 5,980,527 A | 11/1999 | Cohen et al. | |
| 6,017,349 A * | 1/2000 | Heller et al. | 606/92 |
| 6,019,765 A | 2/2000 | Thornhill et al. | |
| 6,019,776 A | 2/2000 | Preissman et al. | |
| 6,024,480 A | 2/2000 | Seaton et al. | |
| 6,033,105 A | 3/2000 | Barker et al. | |
| 6,045,555 A | 4/2000 | Smith et al. | |
| 6,048,346 A | 4/2000 | Reiley et al. | |
| 6,059,790 A | 5/2000 | Sand et al. | |
| 6,066,154 A | 5/2000 | Reiley et al. | |
| 6,083,229 A | 7/2000 | Constantz et al. | |
| 6,086,594 A | 7/2000 | Brown | |
| 6,113,602 A | 9/2000 | Sand | |
| 6,116,773 A | 9/2000 | Murray | |
| 6,116,900 A | 9/2000 | Ostler | |
| 6,120,174 A | 9/2000 | Hoag et al. | |
| 6,120,506 A | 9/2000 | Kohrs et al. | |
| 6,149,655 A | 11/2000 | Constantz et al. | |
| 6,165,219 A | 12/2000 | Kohrs et al. | |
| 6,176,607 B1 | 1/2001 | Hajianpour | |
| D439,980 S | 4/2001 | Reiley et al. | |
| 6,210,031 B1 | 4/2001 | Murray | |
| 6,214,012 B1 | 4/2001 | Karpman et al. | |
| 6,217,581 B1 | 4/2001 | Tolson | |
| 6,235,043 B1 | 5/2001 | Reiley et al. | |
| 6,238,399 B1 | 5/2001 | Heller et al. | |
| 6,241,734 B1 | 6/2001 | Scribner et al. | |
| 6,254,268 B1 | 7/2001 | Long | |
| 6,273,916 B1 | 8/2001 | Murphy | |
| 6,280,456 B1 | 8/2001 | Scribner et al. | |
| 6,293,693 B1 | 9/2001 | Rodgers et al. | |
| D449,691 S | 10/2001 | Reiley et al. | |
| 6,296,149 B1 | 10/2001 | Long | |
| 6,361,539 B1 | 3/2002 | Heller et al. | |
| 6,367,962 B1 | 4/2002 | Mizutani et al. | |
| 6,383,190 B1 | 5/2002 | Preissman | |
| 6,395,006 B1 | 5/2002 | Burchett | |
| 6,395,007 B1 | 5/2002 | Bhatnagar et al. | |
| 6,406,175 B1 | 6/2002 | Marino | |
| 6,423,083 B2 | 7/2002 | Reiley et al. | |
| 6,425,897 B2 | 7/2002 | Overes et al. | |
| 6,431,743 B1 | 8/2002 | Mizutani et al. | |
| 6,435,705 B1 | 8/2002 | Long | |
| 6,439,439 B1 | 8/2002 | Rickard et al. | |
| 6,440,138 B1 | 8/2002 | Reiley et al. | |
| 6,458,136 B1 | 10/2002 | Allard et al. | |
| 6,468,279 B1 | 10/2002 | Reo | |
| D467,657 S | 12/2002 | Scribner | |
| 6,488,651 B1 | 12/2002 | Morris et al. | |
| 6,502,608 B1 | 1/2003 | Burchett et al. | |
| D469,871 S | 2/2003 | Sand | |
| D472,323 S | 3/2003 | Sand | |
| 6,536,937 B1 | 3/2003 | Burchett | |
| 6,547,432 B2 | 4/2003 | Coffeen et al. | |
| 6,550,957 B2 | 4/2003 | Mizutani et al. | |
| 6,558,390 B2 | 5/2003 | Cragg | |
| 6,572,256 B2 | 6/2003 | Seaton et al. | |
| 6,575,919 B1 | 6/2003 | Reiley et al. | |
| 6,582,439 B1 | 6/2003 | Sproul | |
| 6,592,247 B1 | 7/2003 | Brown et al. | |
| 6,599,293 B2 | 7/2003 | Tague | |
| 6,607,544 B1 | 8/2003 | Boucher et al. | |
| 6,610,091 B1 | 8/2003 | Reiley | |
| 6,613,054 B2 | 9/2003 | Scribner et al. | |
| 6,623,505 B2 | 9/2003 | Scribner et al. | |
| 6,626,912 B2 | 9/2003 | Speitling | |
| D482,787 S | 11/2003 | Reiss | |
| 6,641,587 B2 | 11/2003 | Scribner et al. | |
| 6,648,499 B2 | 11/2003 | Jonsson | |
| D483,495 S | 12/2003 | Sand | |
| 6,655,828 B2 | 12/2003 | Vendrely | |
| 6,663,647 B2 | 12/2003 | Reiley et al. | |
| 6,663,669 B1 | 12/2003 | Reiley | |
| 6,673,116 B2 | 1/2004 | Reiley | |
| 6,676,664 B1 * | 1/2004 | Al-Assir | 606/94 |
| 6,702,455 B2 | 3/2004 | Vendrely | |
| 6,709,149 B1 | 3/2004 | Tepic | |
| 6,719,761 B1 | 4/2004 | Reiley et al. | |
| D490,159 S | 5/2004 | Sand | |
| 6,736,537 B2 | 5/2004 | Coffeen | |
| 6,802,822 B1 * | 10/2004 | Dodge | 604/82 |
| 6,910,799 B2 | 6/2005 | Renfro | |
| 6,953,461 B2 * | 10/2005 | McClurken et al. | 606/51 |
| 6,974,247 B2 | 12/2005 | Frei et al. | |
| 7,112,205 B2 * | 9/2006 | Carrison | 606/92 |
| 2001/0011174 A1 | 8/2001 | Reiley et al. | |
| 2002/0013553 A1 | 1/2002 | Pajunk et al. | |
| 2002/0013600 A1 | 1/2002 | Scribner et al. | |
| 2002/0026195 A1 | 2/2002 | Layne et al. | |
| 2002/0082608 A1 | 6/2002 | Reiley et al. | |
| 2002/0099385 A1 | 7/2002 | Ralph et al. | |
| 2002/0156482 A1 | 10/2002 | Scribner et al. | |
| 2002/0156483 A1 | 10/2002 | Voellmicke et al. | |
| 2002/0161373 A1 | 10/2002 | Osorio et al. | |
| 2002/0169471 A1 | 11/2002 | Ferdinand | |
| 2002/0183778 A1 | 12/2002 | Reiley et al. | |

| | | |
|---|---|---|
| 2002/0188299 A1 | 12/2002 | Reiley et al. |
| 2003/0004530 A1 | 1/2003 | Reo et al. |
| 2003/0012079 A1 | 1/2003 | Coffeen et al. |
| 2003/0012080 A1 | 1/2003 | Coffeen et al. |
| 2003/0014056 A1 | 1/2003 | Tague et al. |
| 2003/0032963 A1 | 2/2003 | Reiss et al. |
| 2003/0032964 A1 | 2/2003 | Watkins et al. |
| 2003/0109884 A1 | 6/2003 | Tague et al. |
| 2003/0130664 A1 | 7/2003 | Boucher et al. |
| 2003/0191414 A1 | 10/2003 | Reiley et al. |
| 2003/0191489 A1 | 10/2003 | Reiley et al. |
| 2003/0195547 A1 | 10/2003 | Scribner et al. |
| 2003/0220648 A1 | 11/2003 | Osorio et al. |
| 2003/0220649 A1 | 11/2003 | Bao |
| 2003/0225378 A1 | 12/2003 | Wilkie |
| 2003/0229372 A1 | 12/2003 | Reiley et al. |
| 2004/0030345 A1 | 2/2004 | Aurin et al. |
| 2004/0066706 A1 | 4/2004 | Barker et al. |
| 2004/0122438 A1 | 6/2004 | Abrams |
| 2004/0193171 A1 | 9/2004 | DiMauro et al. |
| 2005/0111299 A1 | 5/2005 | Frei |
| 2006/0052794 A1 | 3/2006 | McGill |

FOREIGN PATENT DOCUMENTS

| | | |
|---|---|---|
| GB | 2338428 | 12/1999 |
| WO | WO97/28835 A1 | 8/1997 |
| WO | WO 2005/000138 | 1/2005 |
| WO | WO 2005/000138 A1 | 1/2005 |

OTHER PUBLICATIONS

PCT International Search Report for PCT/US2005/020925, Applicant: Boston Scientific Scimed, Inc., Form PCT/ISA/210, dated Aug. 10, 2006 (5 pages).

PCT Written Opinion of the International Searching Authority for PCT/US2005/028925, Applicant: Boston Scientific Scimed, Inc., Form PCT/ISA/237) dated Aug. 10, 2006 (5 pages).

Amendment Response to Non-final Office Action mailed Dec. 21, 2005, for related U.S. Appl. No. 10/716,641 submitted Mar. 21, 2006, Inventor Joseph Eder (15 Pages).

Final Office Action for related U.S. Appl. No. 10/716,641 mailed May 19, 2006, Inventor Joseph Eder (5 Pages).

Response to Final Office Action mailed May 19, 2006, for related U.S. Appl. No. 10/716,641 dated Aug. 18, 2006, Inventor Joseph Eder (14 Pages).

Non-final Office Action for related U.S. Appl. No. 10/716,641 mailed Oct. 10, 2006, Inventor Joseph Eder (6 Pages).

Non-final Office Action for related U.S. Appl. No. 10/716,641 mailed Jan. 16, 2007, Inventor Joseph Eder (14 Pages).

Final Office Action for related U.S. Appl. No. 10/716,641 mailed Mar. 22, 2007, Inventor Joseph Eder (6 Pages).

Non-final Office Action for related U.S. Appl. No. 10/922,746, mailed Aug. 14, 2007, Inventor Scott McGill (5 Pages).

Non-final Office Action for related U.S. Appl. No. 10/956,249 dated Dec. 28, 2006, Inventor Scott McGill (11 Pages).

Papers from File History for related U.S. Appl. No. 10/956,249, filed Sep. 30, 2004, 91 pages, including: Amendment Response to Office Action dated Dec. 28, 2006, Response submitted on Apr. 4, 2007 Supplemental Amendment Response to Office Action dated Dec. 28, 2006, Response submitted on Jan. 7, 2008 Office Action dated Jun. 23, 2009 Amendment Response to Office Action dated Jun. 23, 2009, Response submitted on Sep. 17, 2009 Final Office Action dated Jan. 20, 2010 Amendment Response to Final Office Action dated Jan. 20, 2010, Response submitted on Apr. 16, 2010 Office Action dated Aug. 4, 2010 Amendment Response to Office Action dated Aug. 4, 2010, Response Submitted on Oct. 29, 2010 Final Office Action dated Dec. 29, 2010.

Papers from File History for related U.S. Appl. No. 10/922,746, filed Apr. 28, 2009, 41 pages, including: Amendment Response to Office Action dated Aug. 14, 2007, Response submitted on Nov. 26, 2007 Final Office Action dated Feb. 22, 2008 Amendment Response to Final Office Action dated Feb. 22, 2008, Response submitted on May 25, 2008 Office Action dated Jun. 26, 2008 Amendment Response to Office Action dated Jun. 26, 2008, Response submitted on Oct. 20, 2008.

* cited by examiner

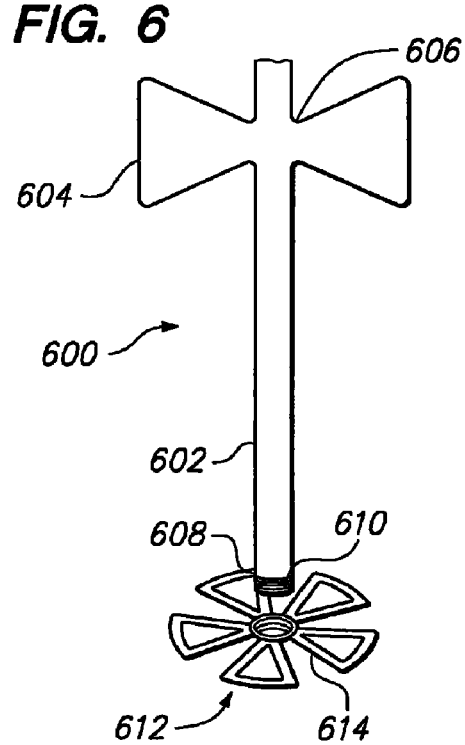
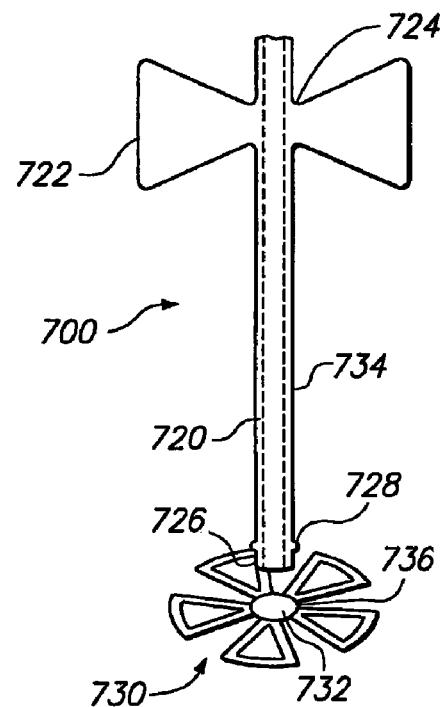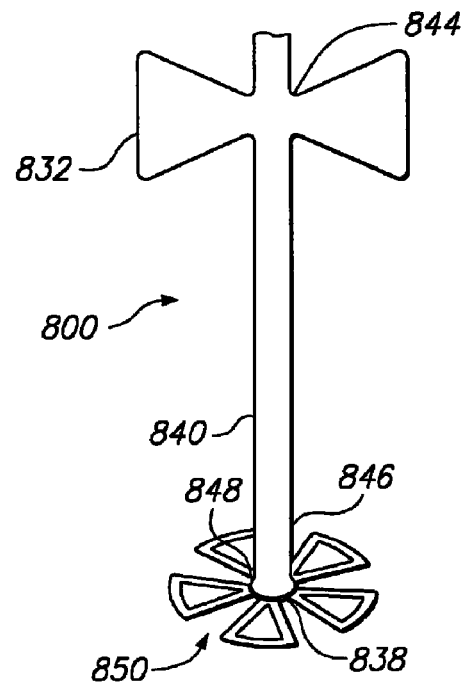

APPARATUS AND METHODS FOR DELIVERING COMPOUNDS INTO VERTEBRAE FOR VERTEBROPLASTY

BACKGROUND OF THE INVENTION

1. Field of the Invention

The invention relates generally to apparatus and methods for delivering compounds into a body, and more particularly to apparatus and methods for delivering bone cement, biomaterials, and/or other flowable compounds into vertebrae, e.g., during a vertebroplasty procedure.

2. Background of the Invention

Vertebroplasty is a procedure during which bone cement, biomaterials, and/or other flowable compounds are delivered into a vertebra. A syringe or other delivery device is generally provided within which the bone cement to be delivered is stored shortly before the bone cement is to be delivered. For example, the delivery device may include a barrel or housing including an open inlet end and an exit end with a narrow outlet. A plunger or threaded driver may be advanced into the inlet end to force bone cement within the barrel out the outlet in the exit end.

A cannula may be inserted percutaneously through the cutaneous layers of tissue above a hard tissue structure being treated and into the hard tissue structure. For example, the hard tissue structure may be a vertebra, and the cannula may include a sharpened tip to penetrate through cortical bone and into the cancellous bone within the vertebra. Alternatively, the hard tissue structure may be exposed using conventional surgical procedures before inserting the cannula and/or the cannula may be inserted over a needle previously placed or simultaneously advanced into the vertebra.

A semi-rigid or flexible tube, e.g., twenty to fifty centimeters long, may be connected between the proximal end of the cannula and the outlet of the delivery device to deliver bone cement via the tube into the hard tissue structure, e.g., to keep the user's hands and/or the delivery device out of the field of an imaging device, such as a fluoroscope, that may be used to monitor the procedure. The tube may be bent slightly during the procedure to lessen the stress that on the cannula and to aid in ensuring the user's hands and/or the delivery device is kept out of the field of an imaging device that may be used during the procedure.

Alternatively, the syringe may be connected directly to the proximal end of the cannula. Such a rigid connection, however, requires a user to support the syringe/cannula combination, which may expose the user to x-ray radiation, e.g., from a fluoroscope used to monitor the injection of the material as it is being injected, requiring the user to wear appropriate additional x-ray protection, which may be cumbersome, inconvenient, and ineffective.

In addition, because of the high viscosity of bone cement, high pressures are generally required to inject bone cement from the delivery device, through the tube and cannula, and into the hard tissue structure. For example, pressures of up to one to three thousand pounds per square inch (1,000-3,000 psi) may be required to inject bone cement from the delivery device. This requires the user to apply substantial force, while simultaneously supporting the weight of the delivery device and its contents. This may cause fatigue of the user and/or undesired movement of the cannula delivery device during the procedure A variety of apparatus and methods for delivering bone cement have been disclosed. Such devices are disclosed in U.S. patent application Ser. No. 10/463,757 filed on Jun. 17, 2003, which is hereby incorporated by reference in its entirety for all purposes as if fully set forth herein.

Accordingly, additional apparatus and methods for delivering bone cement or other compounds into vertebrae would be useful.

SUMMARY OF THE INVENTION

The invention is directed to apparatus and methods for delivering compounds into a body, and more particularly to apparatus and methods for delivering bone cement, biomaterials, and/or other flowable compounds into vertebrae, e.g., during a vertebroplasty procedure.

In one embodiment, the apparatus includes a cannula, sized for insertion into a vertebrae. The cannula has a proximal end, and a distal end, both the distal end and the proximal end are open and a lumen extends therethrough. The apparatus also includes a mix and deliver device with a barrel having a distal end and a proximal end, which defines a cavity for mixing a flowable compound therein, the distal end has an outlet in fluid communication with the cavity. A hollow pivot connector connects the mix and deliver device to the cannula. The pivot connector has a first and a second segment, the two segments allow the pivot connector to rotate about two different axis.

In one embodiment, the apparatus includes a mix and deliver device having a barrel with a distal end and a proximal end, which, define a cavity for mixing a flowable compound therein. The distal end has an outlet in fluid communication with the cavity. A piston is slidably disposed within the cavity of the barrel. A mixing rod is also included.

In one embodiment, the apparatus includes a first barrel defining a first cavity with a distal end, a proximal end and a fluid communication port, where a first piston is slidably disposed with the first cavity. The apparatus also includes a second barrel defining a second cavity with a distal end, a proximal end, and an outlet port, where a second piston is slidably disposed within the second cavity.

In one embodiment the apparatus includes a barrel with a distal end and a proximal end thereby defining a cavity and a fluid communication port located at the distal end. A plunger is disposed with the cavity of the barrel and a trigger element is coupled to the plunger.

In one embodiment the apparatus includes a barrel with a distal end and a proximal end thereby defining a cavity and a fluid communication port located at the distal end. A screw piston is disposed with the cavity of the barrel and a threaded connector is located at the proximal end of the barrel, the connector mates with the screw piston.

In one embodiment, the apparatus includes an introducer with a proximal end and a distal end defining a cavity within which a liquid may be contained. The apparatus also includes a mix and delivery device with a proximal end and a distal end defining a cavity within which a slideable piston is disposed and where the distal end has inlet port. A mixing rod, having a shaft a proximal end and a distal end where the proximal end and the distal end are open and where a lumen extends therethrough, is configured to provide fluid communication between the introducer and the mix and delivery device.

The invention also includes a method for mixing and delivering a flowable compound. The method includes placing a liquid component and a powder component in a cavity of a mix and deliver device; mixing the liquid component and the powder component together; connecting a pressure delivery device to a proximal end of the mix and delivery device; connecting a cannula, inserted into a hard tissue structure, to a distal end of the mix and deliver device; activating the pressure delivery device to deliver a pressure to the mix and deliver device; and delivering the mixed liquid and powder component to the cannula.

In one method for mixing and delivering a flowable compound, the method includes placing a liquid component and a powder component in a cavity of a mix and deliver device; mixing the liquid component and the powder component together; connecting a pressure delivery device to a proximal end of the mix and delivery device by use of a tube; connecting a cannula, inserted into a hard tissue structure, to a distal end of the mix and deliver device; activating the pressure delivery device to deliver a pressure to the mix and deliver device; and delivering the mixed liquid and powder component to the cannula.

In one method mixing a flowable compound includes: connecting a first device containing a liquid component to a second device containing a powder component; reducing the pressure in the second device; drawing the liquid component from the first device into the second device; and mixing the liquid component and powder component together.

Other objects and features of the invention will become apparent from consideration of the following description taken in conjunction with the accompanying drawing.

BRIEF DESCRIPTION OF THE DRAWINGS

The drawings illustrate the design and utility of embodiments of the invention, in which similar elements are referred to by common reference numerals and in which:

FIGS. 6-8 are side views of embodiments of mixing rods with detachable mixing elements in accordance with the invention.

DETAILED DESCRIPTION OF THE ILLUSTRATED EMBODIMENTS

Figure 1:
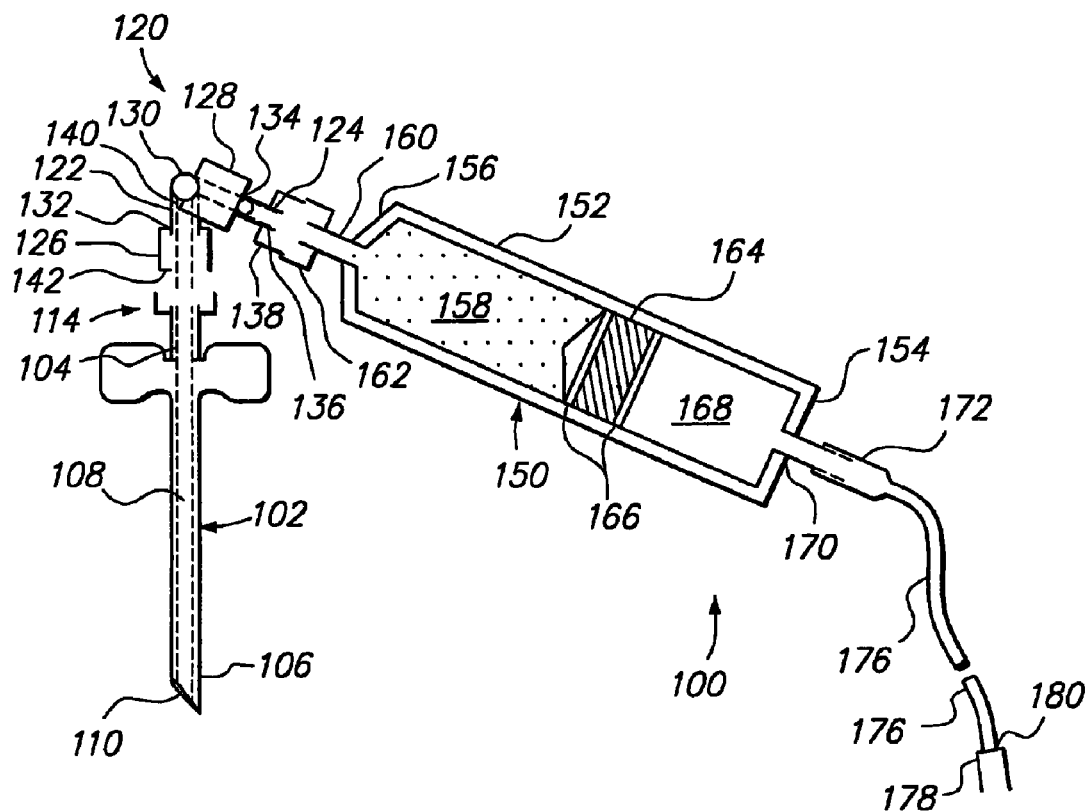
FIG. 1 is a partial cross-sectional side view of an embodiment of an apparatus for delivering bone cement into a vertebra, in accordance with the invention.

Various embodiments of the invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the invention is not necessarily limited to that embodiment and can be practiced in any other embodiments of the invention.

Turning to the drawings, FIG. 1 shows an embodiment of an apparatus 100 for delivering bone cement, biomaterial, and/or other compounds into a vertebra or other hard tissue structure (not shown). Generally, the apparatus 100 includes a cannula 102, a syringe or other delivery device 150, a pivot fitting 120 for pivotally connecting the cannula 102 to the syringe 150, and a tubing 176.

Generally, the cannula 102 is a substantially rigid elongate tubular member including a proximal end 104, a distal end 106, and a lumen 108 extending there through. The cannula 102 may be a needle, i.e., including a beveled or otherwise sharpened distal tip 110 such that the distal end 106 may penetrate into hard tissue, such as bone, although alternatively the cannula 102 may have a substantially blunt distal tip (not shown) and initial access into the hard tissue may be made through other means with the cannula 102 being inserted thereafter. A cannula connector 114 such as a luer fitting may be provided at the proximal end 104 for attaching the cannula 102 to a pivot fitting 120, as described further below.

The cannula 102 may have a substantially uniform diameter or cross-section, similar to known needles for accessing a vertebra, e.g., between about eleven and thirteen gauge (11-13 GA). Alternatively, the cannula 102 may taper from the proximal end 104 at least partially towards the distal end 106, e.g., such that the distal end 106 corresponds to a conventional needle diameter. The cannula 102 may be formed from conventional materials, e.g., stainless steel, metals, plastics, and laminated tubes.

The pivot fitting 120 generally includes a first and a second section, each comprising a tubular segment, i.e., a first tubular segment 122 and a second tubular segment 124, and a corresponding hollow housing, i.e., a first hollow housing 122 and a second hollow housing 124, that are pivotally coupled to one another. The first tubular segment 122 may include a first end 130 coupled to the second hollow housing 128 and a second end 132 terminating in the first hollow housing 126, the first and the second hollow housings 126, 128 may be connectors, e.g., male or female luer lock connectors which are designed to mate for example with the connector 114 on the cannula 102. The first hollow housing 126 may include a socket (not shown) for receiving the second end 132 of the first tubular segment 122 such that the tubular segment 122 is free to pivot relative to the first hollow housing 126. The pivoting action may allow the syringe 150 to rotate inline with a central axis of the cannula 102. This rotation assists in the placement of the syringe 150 in a location relative to a treatment site that is best suited to minimize interference with the procedure.

The second tubular segment 124 may include a first end 134 coupled to the second hollow housing 128 and a second end 136 for connecting to the syringe 150. The second end 136 may be constructed in the form of a connector 138 for ease of connection with a connector 162 on the syringe 150. The connectors 114, 126, 138, 162 may be any style that is capable of creating a seal and withstanding the pressure demands, e.g., 1000-3000 psi on the apparatus, e.g., a luer connector with female and male components, or a compression fitting. The second hollow housing 128 may include a socket (not shown) for receiving the first end 134 of the tubular segment 124 such that the tubular segment 124 is free to pivot relative to the second hollow housing 128. The pivoting action may allow the syringe 150 to rotate transverse to a central axis of the second hollow housing 128. The connector 114 may be constructed from multiple parts or may be preassembled and permanently fixed as a unit. This rotation provides for ease of connection of the syringe 150 to the pivot fitting 120. Furthermore, this rotation assists in the placement of the syringe 150 at a suitable angle relative to a body surface thereby minimizing the stress place on the cannula 102 as a result of the weight of the syringe 150. The pivot fitting 120 may be comprised of multiple components that are assembled, alternatively the pivot fitting 120 may be constructed as a single component.

The first and second tubular segments 122, 124 and the first and second hollow housings 126, 128 define a lumen 140 therein that extends from an end 142 of the first hollow housing 126 to the second end 136 of the second tubular segment 124. Preferably, the lumen 140 remains substantially open throughout any pivotal movement of the first or second tubular segments 122, 124. Thus, the lumen 140 may provide a substantially fluid-tight passage that extends between the second end 142 of the first hollow housing 126 and the second end 136 of the second tubular segment 124 through the first and second hollow housings 126, 128 to allow bone cement or other flowable compounds to pass through the pivot fitting 120 without substantial leakage.

The first and second tubular segment 122, 124 and the first and second hollow housings 126, 128 may be formed from any variety of materials, known to those of skill in the art, capable of handling the internal pressures experienced when bone cement is delivered, e.g., between about one and three thousand pounds per square inch (1,000-3,000 psi). In addition, the pivot fitting 120 should be sufficiently strong to support any bending or other forces experienced when the pivot fitting 120 is used to couple a cannula 102 to a syringe 150 during a vertebroplasty procedure.

In alternative embodiments, the pivot fitting 120 may be substantially permanently attached to at least one of the cannula 102 or the syringe 150. For example, the pivot fitting 120 may be provided as part of the syringe 150, i.e., extending from a distal end 156 of the syringe 150, thereby eliminating connectors 162, 138 between the pivot fitting 120 and the syringe 150 (not shown). In this instance, therefore, the other end of the pivot fitting 120 may have a connector 126, as explained above. Alternatively, the pivot fitting 120 may be substantially permanently attached to the proximal end 104 the cannula 102 (also not shown). Thus, one or both ends of the pivot fitting 120 may be detachable from and/or substantially permanently attached to the cannula 102 and/or syringe 150.

With continued reference to FIG. 1, the syringe 150 generally includes a barrel 152 including a proximal end 154, and a distal end 156, thereby defining an interior space or cavity 158 within which a flowable compound, such as bone cement and/or biomaterials (not shown), may be contained. The distal end 156 may include an outlet port 160 that is in fluid communication with the cavity 158. A luer lock or other connector 162 may be provided on the outlet port 160 for cooperating with a complementary connector, such as the connector 138 on the pivot fitting 120 as described above.

A piston 164 may be slidably disposed near the proximal end 154 of the barrel 152 within the cavity 158 for forcing a compound within the barrel 152 out through the outlet port 160. The piston 164 may be advanced distally, as described below, thereby applying a force creating sufficient pressure to push the compound within the barrel 152 out the outlet port 160. Optionally, the piston 164 may include a nipple (not shown) extending into the cavity 158. The nipple may have a size corresponding to the outlet port 160 of the syringe 150, e.g., such that the nipple may be slidably received in the outlet port 160 as the piston 164 is slidably forced toward the distal end 156. The nipple may minimize the amount of bone cement remaining within the syringe 150 when the piston 164 has reached the distal end 156 of the barrel 152. Furthermore, the piston 164 may include gaskets 166 such as o-rings designed to ensure a tight seal between the piston 164 and the barrel 152 while also preventing any contamination of the bone cement (not shown), that is located in the cavity 516, with a fluid or gas that may be located on the input pressure or hydraulic side in the proximal section 168 of the barrel cavity 158. The syringe 150 may be constructed from any materials known to those of skill in the art, for example, the syringe 150 may be constructed from Cyclic Olefin Copolymers (COC), Polycarbonate, Polystyrene, plastics, metals, or any variety of surgical metals.

Preferably, the proximal end 154 of the barrel 152 is substantially closed but includes an opening 170 through which an actuating device (not shown), may be connected to the barrel 152, for delivering a fluid, gas or driving rod into the proximal section 168 of the barrel cavity 158. Connection of an actuating device to the syringe 150 may be made through a connector 172 attached to the opening 170 on the syringe 150 that mates with the connector 172 on a tubing 176. The tubing 176 is then connected to an actuating device through a connector 178. The actuating device delivers a fluid, e.g., saline or a gas through the tubing 176 into the proximal section 168 of the barrel cavity 158 to cause the piston 164 to slide distally within the cavity 158. The tubing 176, and opening 170 may include integral connectors as opposed to connectors as described above. Alternatively, the tubing 176 may be substantially permanently attached to the syringes 150.

The actuating device may comprise a pump or other device such as those described below in conjunction with FIGS. 10-12 to advance the piston 164 and inject bone cement into the cannula 102 by delivering a fluid or gas through the tubing 176 into the proximal chamber 168. This forces the piston 164 distally, thereby forcing the bone cement out of the cavity 158 and into and/or through the pivot fitting 120 and cannula 102.

The tubing 176 may vary from being a semi-rigid elongated member to being a relatively compliant flexible tube. For example the tubing may be polyurethane, or braid or coil reinforced catheter materials, PEEK or polyamide or metal. The tubing 176 preferably has sufficient length such that a proximal end 180 of the tubing 176 may be disposed away from a patient, and preferably away from a field of an imaging device, e.g., fluoroscope, as explained further below. For example, the tubing 176 may have a length between about ten and seventy centimeters (10-70 cm). Furthermore, the tubing 176 must have sufficient cross-sectional strength to withstand the delivery pressures as described above. The tubing 176 may be constructed from any material known to those of skill in the art for example, the tubing may be formed from PEEK or polyimide.

In order to deliver bone cement or other biomaterials, the cannula must be inserted into the vertebra (not shown). If the distal end 106 of the cannula 102 includes a sharpened distal tip 110, the distal tip 110 may be inserted directly into a vertebra, e.g., until the distal end 106 penetrates the cortical bone and enters the cancellous bone region therein. The cannula 102 may be inserted percutaneously, e.g., through cutaneous fat, muscle, and/or other tissue overlying the vertebra. Alternatively, the vertebra may be at least partially exposed before inserting the cannula 102, e.g., using an open surgical procedure. For example, the tissue overlying the vertebra may be surgically dissected and/or retracted to expose the vertebra, and the distal end 106 of the cannula 102 may be inserted into the exposed vertebra.

In one embodiment (if the cannula 102 is initially separate from the pivot fitting 120 and/or the syringe 150), a stylet, an obturator or other device (not shown) may be inserted into the lumen 108 of the cannula 102 to prevent tissue and/or fluid, such as blood, from entering the lumen 108 while the cannula 102 is advanced through tissue. In a further alternative, a stylet and sheath (also not shown) may be percutaneously inserted through overlying tissue to access the vertebra. The stylet may be removed from within the sheath, and the cannula 102 may be advanced through the sheath and then inserted into the vertebra.

It will be appreciated that any known open or minimally invasive procedure may be used to place the cannula 102 into the vertebra. In addition, it will be appreciated that the insertion of the cannula 102 may be monitored using external imaging, such as fluoroscopy, ultrasound imaging, magnetic resonance imaging ("MRI"), and the like (not shown). For example, the cannula 102 may be formed from radiopaque material and/or may include one or more radiopaque markers to facilitate monitoring the position of the cannula 102 as it is advanced into the vertebra using a fluoroscope, as is known in the art.

Once the distal end 106 of the cannula 102 is inserted into the vertebra the syringe 150 (with bone cement or other compound provided therein using conventional methods) may be connected to the proximal end 104 of the cannula 102. For example, the pivot fitting 120 may be connected first (or, alternatively, may be substantially permanently attached) to the distal end 156 of the syringe 150, for example, the outlet port 160. The loose end of the pivot fitting 120 (e.g., the second end 132 of the first tubular segment 122) may be connected to the proximal end 104 of the cannula 102, e.g., by connecting mating luer lock connectors 114, 126.

Alternatively, the pivot fitting 120 may be substantially permanently attached to the proximal end 104 of the cannula 102, and then may be attached to the distal end 156 of the syringe 150, e.g., using mating luer lock connectors 162, 138. In a further alternative, the pivot fitting 30 may be substantially permanently attached to both the cannula 102 and the syringe 150 (not shown), such that the syringe 150 is attached to the cannula 102 when the cannula 102 is inserted into the vertebra.

Once the apparatus 100 is assembled, the syringe 150 may be disposed at a desired angle relative to the cannula 102. For example, it may be desirable to lay the syringe 150 on the patient's skin (e.g., on the patient's back) overlying the vertebra. The syringe 150 may be supported by a stand (not shown) so that an optimal angle, relative to the patients skin is obtained. The stand may be integral to the syringe 150 or may be a separate piece that supports the syringe 150. The stand may help to remove the weight of the syringe 150 and its contents from the cannula 102, thereby further minimizing the risk of bending or otherwise damaging the cannula 102.

Because the syringe 150 may be located within the field of an imaging system, e.g., a fluoroscope (not shown), it may be desirable to extend the tubing 176 away from the patient's body, until an actuating device (not shown) is located outside the field of the imaging system. This will remove the operator away from the field, thereby substantially reducing their exposure to radiation and the like.

Once the syringe 150 is disposed at a desired location, the piston 164 may be advanced to deliver the bone cement or other compound from the syringe 150 through the pivot fitting 120 and the cannula 102 into the cancellous bone region of the vertebra. Because the path through which the bone cement passes is substantially shorter than the path when conventional tubing is used to connect a syringe to a cannula (not shown), less pressure may be required to deliver the bone cement than using such tubing systems. In addition, less bone cement may be wasted, because the flow path may have less volume that must be filled with bone cement before the bone cement exits the cannula 102 and enter the vertebra.

Once sufficient bone cement is delivered into the vertebra, the cannula 102 may be removed and the puncture or other access opening may be closed using conventional procedures.

It may be desirable to keep the connector 162 at the distal end 156 of the syringe 150 clean and free from any bone cement to ensure an uncontaminated and tight connection between the syringe 150 and the pivot fitting 120. It is possible that some bone cement may have bled out of the syringe 150 and into the connector 162, for example when removing air from the syringe as discussed below. To ensure a clean connection is attained, a tool may be provided to clean the connector 162 prior to connecting the syringe 150 to the pivot fitting 120. Alternatively, an additional piece may be attached to the connector 162. The piece is then removed prior to connecting the syringe 150 to the pivot fitting 120, thereby keeping the connector 162 clean.

Figure 2:
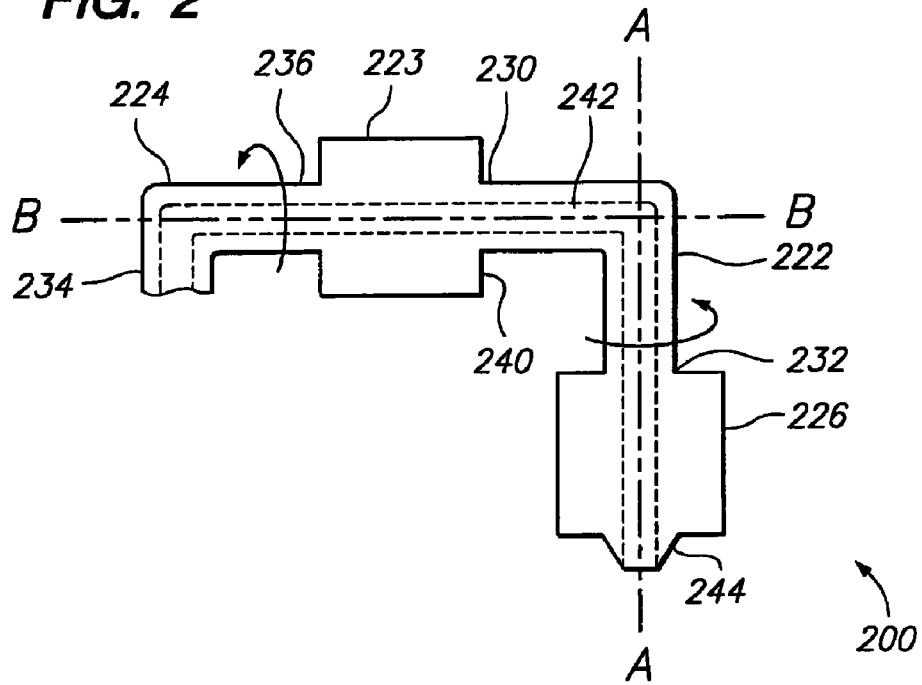
FIG. 2 is a side view of a pivot fitting for use with the apparatus of FIG. 1.

FIG. 2 is a detailed depiction of an exemplary pivot fitting 200 for use with the apparatus of FIG. 1. Generally the pivot fitting 200 includes first and second portions, each comprising a tubular segment, i.e., a first and a second tubular segment 222, 224 and a corresponding hollow housing, i.e., a first and a second hollow housing 226, 228 that are pivotally coupled to one another. The first tubular segment 222 may include a first end 230 terminating in a first end 240 of the second hollow housing 228 and a second end 232 terminating in the first hollow housing 226. The first hollow housing 226 includes a socket (not shown) for receiving the second end 232 of the first tubular segment 222 such that the tubular segment 222 is free to pivot relative to the first hollow housing 226. The first hollow housing may include a connector such as a luer fitting to allow for the connection of the pivot fitting 200 to a cannula (not shown) As illustrated, the first tubular segment 222 rotates about the axis A-A, that lies along a central axis of the first hollow housing 226.

The second tubular segment 224 may include a first end 234 that is connectable to a syringe or other delivery device (not shown) and a second end 236 terminating in the second hollow housing 228. The second hollow housing 228 includes a socket (not shown) for receiving the second end 236 of the second tubular segment 224 such that the tubular segment 224 is free to pivot relative to the second hollow housing 228. As illustrated, the second tubular segment 224 rotates about the axis B-B that lies along a central axis of the second hollow housing 228 and is perpendicular to the axis A-A.

The first and second tubular segments 222, 224 and the first and second hollow housings 226, 228 define a lumen 242 therein that extends between the first end 234 of the second tubular segment 224 to a proximal end 244 of the first hollow housing 226. Preferably, the lumen 242 remains substantially open throughout any pivotal movement of the first or second tubular segments 222, 224. Thus, the lumen 242 may provide a substantially fluid-tight passage to allow bone cement or other flowable compounds to pass through the pivot fitting 200 without substantial leakage.

Figure 3:
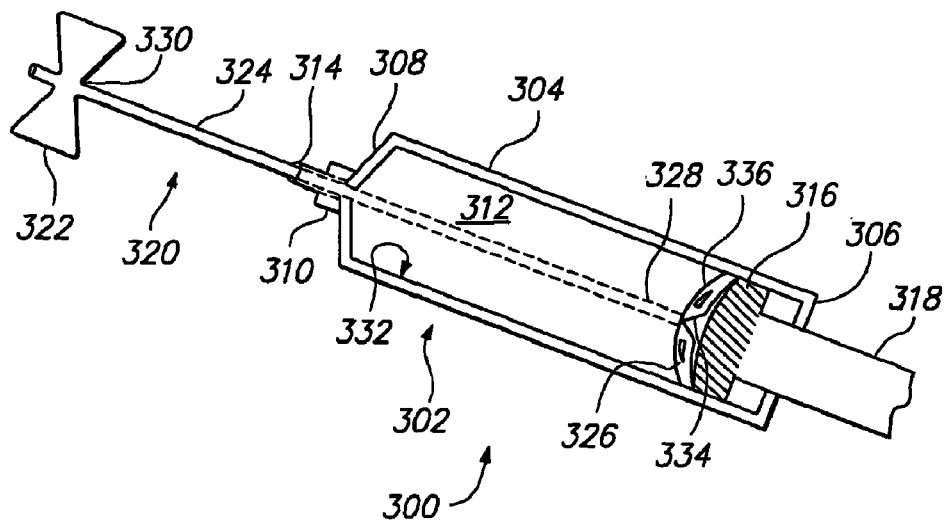
FIG. 3 is a partial cross-sectional side view of an embodiment of an apparatus for mixing bone cement in accordance with the invention.

FIG. 3 illustrates an apparatus 300 for mixing bone cement, and specifically for mixing a two part, i.e., powder and fluid, bone cement. Generally, the apparatus 300 includes a syringe 302 or mixing unit, and a mixing rod 320.

The syringe 302 generally includes a barrel 304 including a proximal end 306, and a distal end 308, thereby defining an interior space or cavity 312 within which a flowable compound, such as bone cement and/or biomaterials (not shown), may be mixed. The distal end 308 may include an outlet port 314 that is in fluid communication with the cavity 312. A luer lock or other connector 310 may be provided on the outlet port 314 for cooperating with a complementary connector, such as the connector 162 on a delivery device 150 so that the flowable compound may be transferred from a mixing syringe 302 to a delivery syringe such as the syringe 150 of FIG. 1.

A piston 316 may be slidably disposed in the proximal end 306 of the barrel 304 within the cavity 312 for forcing a compound within the barrel 304 out through the outlet port 314 after the compound is mixed. Preferably the proximal end 306 of the barrel 304 is constructed so as to substantially seal a piston rod 318 coupled to the piston 316. The piston 316 may be advanced distally, moving the piston 316 toward the distal end 308 by applying a force to the piston rod 318. Optionally, the piston 316 may include a nipple (not shown) extending into the cavity 312. The nipple may have a size corresponding to the outlet port 314 of the syringe 302, e.g., such that the nipple may be slidably received in the outlet port 314 as the piston 316 is slidably forced toward the distal end 308. The nipple may minimize the amount of bone cement remaining within the syringe 302 when the piston 316 has reached the distal end 308 of the barrel 304.

The mixing rod 320 generally includes a shaft 324 having a proximal end 330, and a distal end 328. The shaft 324 may be solid or hollow with an axial lumen extending from the proximal end 330 to the distal end 328. Located at the proximal end 330 of the shaft 324 is a handle 322. At the distal end 328 of the shaft 324 is a mixing element 326. The mixing element 326 preferably has multiple openings to facilitate mixing and is sized such that the mixing element 326 contacts or is in close proximity to the interior surface 332 of the barrel 304 while still being able to slide within the cavity 312. Preferably, the mixing element 326 is shaped so that the proximal surface 334 of the mixing element is substantially flush with the piston 316 when the mixing element abuts the piston, and the distal surface 336 is substantially flush with the distal end 308 of the barrel 304 when the mixing element 326 abuts the distal end 308 of the barrel 304. It is desirable to having the mixing element 326 shaped in this manner to ensure thorough mixing and that no powder remains unmixed in any portion of the barrel 304.

As described above the shaft 324 of the mixing rod 320 may be solid or hollow. If the shaft is solid, the fluid and the powder parts must both be placed in the syringe before the syringe is sealed and before the mixing rod 320 is positioned to blend the liquid and powder components. If the mixing rod 320 has a hollow shaft that is open at the distal end 328 fluid may be inserted into the syringe 302 through the mixing rod 320. If the shaft is hollow, fluid is inserted into the proximal end 330 of the shaft 324 and flows through the shaft and out the distal end 328 of the shaft 324. The shaft 324 may also be constructed with outlet ports (not shown) that allow the fluid to flow out along the length of the shaft (see for example, the detailed description of FIG. 4). Therefore, only the powder part is required to be in the syringe 302 prior to sealing the syringe and positioning the mixing rod. In the latter instance, mixing may begin as the fluid is added to the powder. If the fluid is added through a hollow shaft the outlet port 314 may be designed to allow air to escape as the fluid enters the syringe 302. The outlet port 314 may be designed as a luer connector with airports, or may be a sponge valve that allows air to escape as fluid is inserted or may be designed with any other device that allows air within the cavity 312 to escape as fluid is added.

The fluid and powder (not shown) are mixed in the syringe 300 by moving the mixing element 326 through the barrel 312. The mixing element 326 is moved throughout the barrel 312 by grasping the handle 322 and moving the mixing rod 320 back and forth axially through the barrel. The mixing element 326 may also be rotated along the interior circumference of the barrel 304 by turning slightly the handle 322 either clockwise or counterclockwise or any combination thereof.

The powder may be prepacked in the syringe or may be added to the syringe prior to mixing.

The mixing element and the mixing rod may be constructed from any materials known to those of skill in the art, for example, stainless steel or medical grade plastic. While the mixing element and mixing rod are preferably constructed from the same materials, each may be constructed from different materials.

Figure 4:
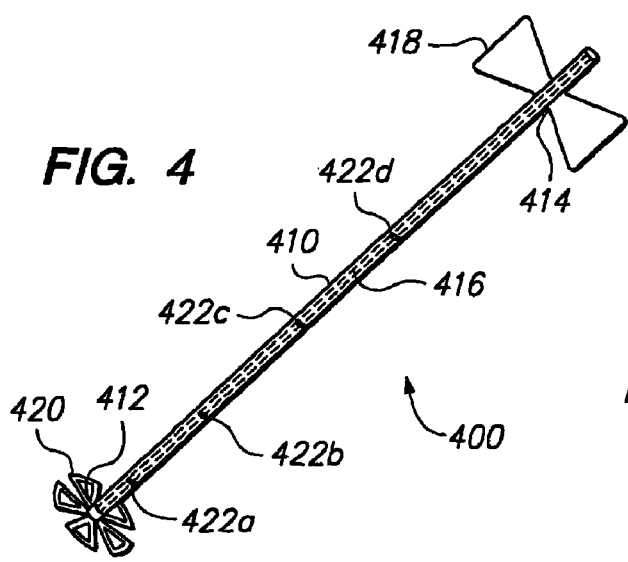
FIG. 4 is a partial cross-sectional side view of a mixing rod for use in the apparatus of FIG. 3 in accordance with the invention.

FIG. 4 illustrates a mixing rod 400 in accordance with an embodiment of the invention. The mixing rod 400 generally comprises a hollow shaft 410 having a distal end 412, a proximal end 414 and an axial lumen 416 there between. Located at the proximal end 414 of the hollow shaft 410 is a handle 418. At the distal end 412 of the hollow shaft 410 is a mixing element 420. The proximal end 414 of the hollow shaft 410 is open to allow fluids (or gases) to enter the axial lumen 416. The distal end 412 of the hollow shaft 410 is sealed to prevent fluids from exiting the axial lumen 416 at the distal end 412.

Located along the axial length of the hollow shaft 410 are lumen access ports 422 (a-d). The lumen access ports 422(a-d) are located along the length and around the circumference of the hollow shaft 410 and provide access to the axial lumen 416. The lumen access ports 422(a-d) allow fluids that have been inserted into the axial lumen 416 of the hollow shaft 410 to exit the hollow shaft 410 at various sites along the hollow shaft 410. While depicted as rectangular opening, the lumen access ports 422 (a-d) could be any variety of shapes. Also, while there are four lumen access ports 422(a-d) depicted, any number of access ports could be created along the length of the hollow shaft 410. Furthermore, while the lumen access ports 422(a-d) are depicted as being the same size, the size of the access ports could vary. For example, the access ports located toward the distal end of the hollow shaft could be larger and those located at the proximal end could be smaller to ensure more uniform dispensing of the fluid.

Figure 5:
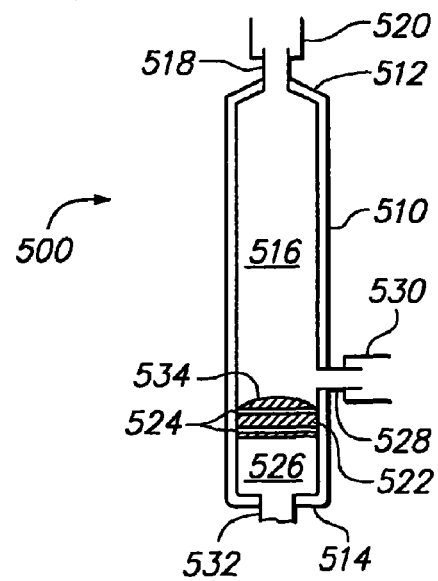
FIG. 5 is a partial cross-sectional side view of an embodiment of an apparatus for delivering bone cement into a vertebra in accordance with the invention.

FIG. 5 is an alternative delivery syringe 500 for mixed bone cement. The syringe 500 generally includes a barrel 510 having a proximal end 514, and a distal end 512, thereby defining an interior space or cavity 516 within which a flowable compound, such as bone cement and/or biomaterials (not shown), may be contained. The distal end 512 may include an outlet port 518 that is in fluid communication with the cavity 516. A luer lock or other connector 520 may be provided on the outlet port 518 for cooperating with a complementary connector, on a pivot fitting as discussed previously.

A piston 522 may be slidably disposed in a proximal portion 526 of the barrel 510 within the cavity 516 for forcing a compound within the barrel 510 out through the outlet port 518. The piston may have gaskets 524 such as o-rings to ensure a tight seal between the piston 522 and the barrel 510 preventing any contamination of the bone cement (not shown)

that is located in the cavity 516 with the fluid or gas that may be located on the pressure or hydraulic side. The piston 522 may be advanced distally, as described below thereby applying a force creating sufficient pressure to inject the compound within the barrel 510 out the outlet port 518.

Preferably, the proximal end 514 of the barrel 510 is substantially closed but includes an opening 532 through which an actuating device (not shown), may be connected to the barrel 510, for delivering a fluid or gas into the proximal section 526 of the barrel cavity 516 as described previously in relation to FIG. 1.

Along the circumference of the barrel 510 there is an inlet port 528. The inlet port 528 is located nearer the proximal portion 526 of the cavity 516. A distal end 534 of the piston 522 is located just below the inlet port 528. A connector 530 may be provided on the inlet port 528 for cooperating with a complementary connector on a mixing unit (not shown). The inlet port 528 is designed to connect with a mixing unit (not shown) to allow for the transfer of bone cement from a mixing unit to the delivery syringe 500.

The transfer of bone cement into a side of a delivery device can help to minimize unwanted air. For example, when the bone cement (not shown) is inserted through the inlet port 528, the cavity 516 is filled from the distal end 534 of the piston 522 upward toward the distal end 512 of the barrel 510. Any air, which remains near the distal end 512, is easily removed before connecting the delivery syringe 500 to the delivery system (not shown) by forcing the piston 522 toward the distal end 512 thereby forcing the air out the outlet port 518.

Alternatively, bone cement could be transferred into a delivery device such as device 500, through the outlet port 518 at the distal end 512 of the barrel 510. After transferring the bone cement, any air remaining in the cavity 516 would be removed by forcing the piston 522 toward the distal end 512.

In any event, it is desirable to remove unwanted air out of the delivery device before connecting the delivery device to the delivery system.

FIGS. 6-8 illustrate various embodiments of mixing rods with detachable mixing elements.

FIG. 6 illustrates a mixing rod 600 having a threaded connection between a shaft 602 and a mixing element 612. The shaft 602 has a proximal end 606 and a distal end 608. Located at the proximal end 606 of the shaft 602 is a handle 604. Located at the distal end 608 of the shaft 602 is screw having advancing spiral threads 610. The mixing element 612 has a central threaded opening 614 for receiving the shaft 602. The central threaded opening 614 is designed to mate with the spiral threads 610 located at the distal end 608 of the shaft 602. In a conventional manner the mixing element 612 can be attached to the shaft 602 by rotating the shaft 602 in a clockwise direction relative to the central threaded opening 614 to engage the spiral threads 610 at the distal end 608 of the shaft with the central threaded opening 614 on the mixing element. Conversely, the shaft 602 can be detached from the mixing element 612 by rotating the shaft 602 counterclockwise relative to the central threaded opening 614 to disengage the spiral threads 610. While described as a central threaded opening 614, the opening could be offset in the mixing element if so desired.

FIG. 7 illustrates a mixing rod 700 having a spring-loaded connection between a shaft 720 and a mixing element 730. The shaft 720 has a proximal end 724 and a distal end 726. Located at the proximal end 724 of the shaft 720 is a handle 722. Located towards the distal end 726 of the shaft 720 is at least one spring-loaded element(s) 728. While the embodiment is depicted as having two spring-loaded elements, this is not intended to be a limitation on the number of spring elements. The mixing element 730 has an opening 732 for receiving the shaft 720. The opening 732 may have complementary grooves 736 for mating with the spring-loaded element(s) 728. As the shaft 720 is inserted through the opening 732 the spring-loaded element(s) 728 are forced to retract into the wall 734 of the shaft 720. Once the distal end 726 of the shaft 720 where the spring-loaded elements 728 are located is aligned with the complementary grooves 736, the spring-loaded elements 728 release and lock into place. Alternatively, the distal end 726 of the shaft 720, where the spring-loaded elements 728 are located, may pass through the opening 732. Once the spring-loaded element(s) 728 have passed through the opening 732, the spring-loaded elements 728 may release thereby preventing the shaft 720 from easily being pulled out. The shaft 720 may be released from the mixing element 730 by exerting a quick thrust such as a force great enough to release the shaft on the shaft 720 in a direction opposite the mixing element 730. This sudden force would pull the shaft 720 up and push the spring-loaded elements back into the wall 734 of the shaft 720.

Alternatively, the shaft 720 could be designed with a button (not shown), coupled to the spring-loaded element(s) 728 through the wall. When pushed, the button would cause the spring-loaded element(s) 728 to retract. When released, the spring-loaded element(s) 728 would extend. If configured in this manner, the locking and release mechanism would still operate in the same mode as described above.

FIG. 8 illustrated a mixing rod 800 having a mechanical interference connection between a shaft 840 and a mixing element 850. The shaft 840 has a proximal end 844 and a distal end 846. Located at the proximal end 844 of the shaft 840 is a handle 832. The distal end 846 of the shaft 840 has a bulge 848. The mixing element 850 has an opening 838 for receiving the shaft 840. The opening 838 is designed to mate with the bulge 848 located at the distal end 846 of the shaft 840. In a conventional manner the mixing element 850 can be attached to the shaft 840 by placing the bulge 848 at the distal end 846 of the shaft 840 into the opening 838 on the mixing element 850. Because a connection of this type requires a tight fit, some force would be necessary to insert to the bulge 848 into the opening 838. Alternatively, the mixing rod 800 and mixing element 850 could be preassembled thereby eliminating the assembly step. The shaft 840 is detached from the mixing element 850 by exerting a force in a direction proximal the mixing element 850 causing the bulge 848 to release from the opening 838.

FIGS. 6-8 describe various embodiments of mixing rods with detachable mixing elements, the embodiments shown are not intended to be a limitation of the various means by which the mixing element may be detached from the rod. Furthermore, the mixing element may be detached from the rod by simply breaking off the rod. A mixing rod constructed in this manner would be designed with an inherent weak joint such that the rod would break at the distal end of its length. This break-away could be accomplished by pulling the rod toward a distal end of a mixing device and then exerting a lateral force on the rod causing it to break at the weak joint thereby disengaging the rod form the mixing element.

One advantage of using a mixing rod of the type described in conjunction with FIGS. 6-8 is that one device, i.e. a syringe, may be used for both mixing the flowable compound and delivering the flowable compound.

Figure 9A:
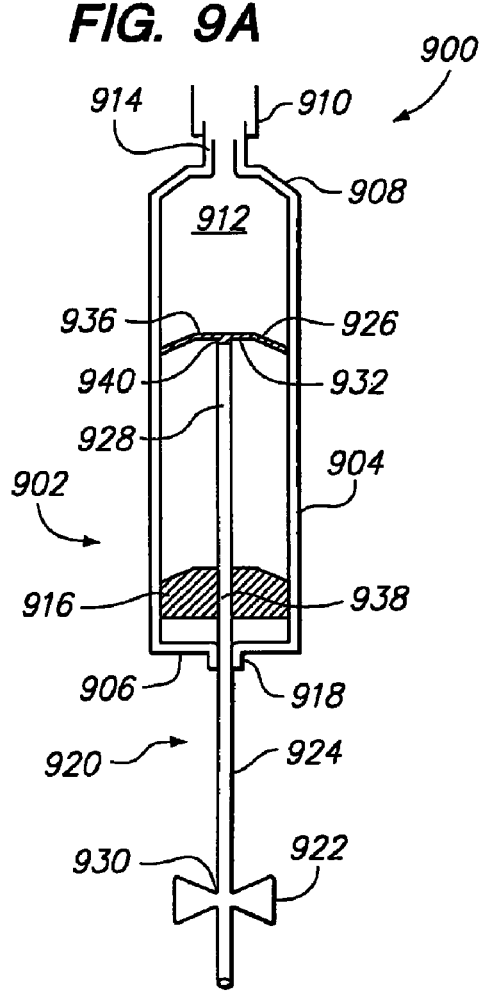
FIGS. 9A and 9B are partial-cross sectional views of another embodiment of an apparatus for mixing bone cement in accordance with the invention.
Figure 9B:
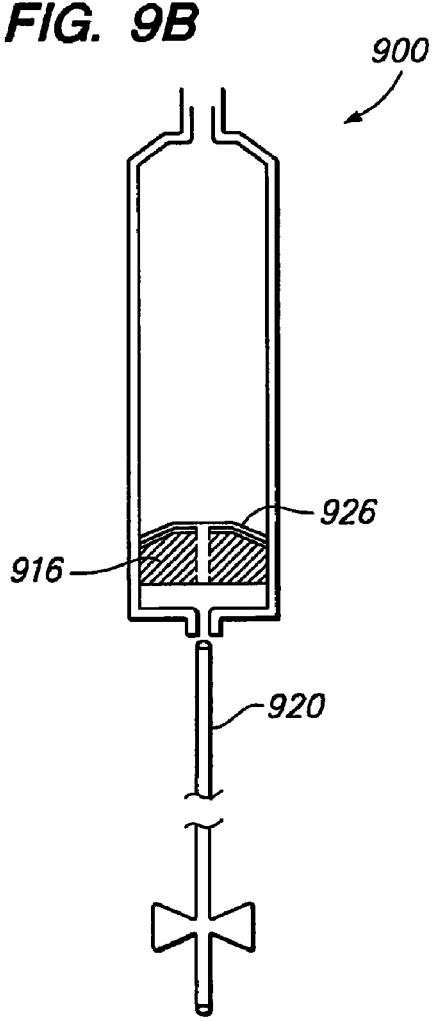

FIGS. 9A and 9B illustrate an apparatus 900 for mixing bone cement where a mixing rod is inserted from a proximal end of the apparatus. Generally, the apparatus 900 includes a syringe 902 or mixing unit, and a mixing rod 920.

The syringe 902 generally includes a barrel 904 including a proximal end 906, and a distal end 908, thereby defining an interior space or cavity 912 within which a flowable compound, such as bone cement and/or biomaterials (not shown), may be mixed. The distal end 908 may include an outlet port 914 that is in fluid communication with the cavity 912. A luer lock or other connector 910 may be provided on the outlet port 914 for cooperating with a complementary connector, such as the connector 162 on a delivery device 150 as discussed above. During the mixing process, the outlet port 914 is capped so that the flowable compound does not leak out.

A piston 916 may be slidably disposed in the proximal end 906 of the barrel 904 within the cavity 912 for forcing a compound within the barrel 904 out through the outlet port 914 after the compound is mixed. At the proximal end 906 of the barrel 904 there is an inlet port 918.

The mixing rod 920 generally includes a shaft 924 having a proximal end 930, and a distal end 928. The shaft 924 may be solid or hollow as discussed above in conjunction with FIG. 3. Located at the proximal end 930 of the shaft 924 is a handle 922. At the distal end 928 of the shaft 924 is a mixing element 926. The mixing element 926 may also forms a distal end of the piston 916. The mixing element 926 is preferably designed as described in FIG. 3 above. Furthermore, the mixing element 926 is shaped so that the proximal surface 932 of the mixing element is substantially flush with the piston 916 when the mixing element abuts the piston, thereby becoming the distal end of the piston 916. Preferably, the distal surface 936 is substantially flush with the distal end 908 of the barrel 904 when the mixing element 926 abuts the distal end 908 of the barrel 904.

In this embodiment, the shaft 924 of the mixing rod 920 is inserted into an inlet port 918 of the barrel 904 and through a lumen 938 of the piston 916. The shaft 924 is then coupled to the mixing element 926, which forms the distal end of the piston 916. The mixing element 926 is constructed such that at a central junction of the mixing element 926 and the shaft 924 the mixing element has a solid plug like extension 940. When the mixing element 926 is not in use, it is located at and may form the distal end of the piston 916, the extension 940 seals a distal end of the lumen 930 of the piston 916.

The mixing element 926 may be attached to and detached from the shaft 924 in a variety of ways, such as those described in conjunction with FIGS. 6-8 above.

Mixing of the fluid and powder is performed as described previously in conjunction with FIG. 3. Once the mixing rod shaft 924 is removed from barrel 904. The mixing unit may then be used as a delivery device such as the syringe 150 as described in FIG. 1, or the syringe 902 may be used to deliver the mixed compound into another delivery device.

Figure 10:
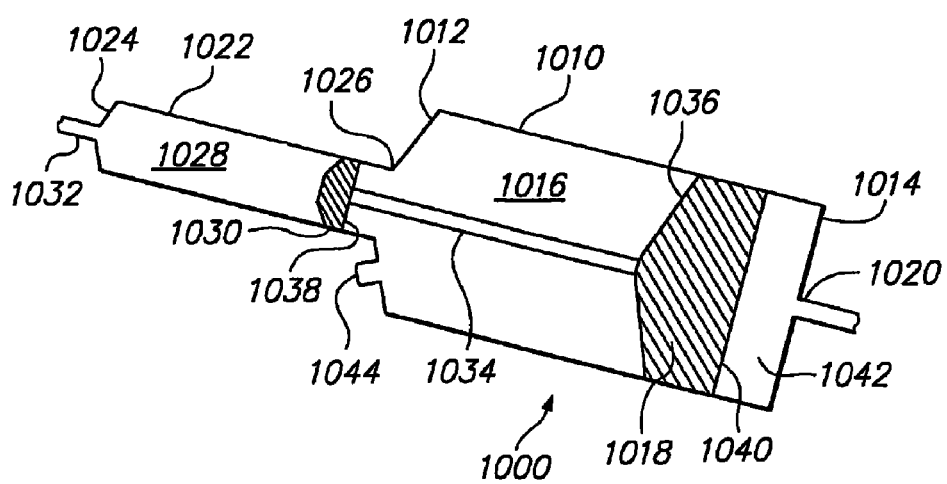
FIG. 10 is a partial cross-sectional side view of an actuator for use with the apparatus of FIG. 1.

FIG. 10 illustrates an actuator 1000 in accordance with an embodiment of the invention. The actuator 1000 generally includes a first barrel 1010 including a proximal end 1014, a distal end 1012, and fluid communication port 1020, thereby defining a first interior space or cavity 1016 and a second barrel 1022 including a proximal end 1026 and a distal end 1024 thereby defining a second interior space or cavity 1028.

A first piston 1018 may be slidably disposed in the proximal end 1014 of the first barrel 1010 within the first cavity 1016. Preferably the proximal end 1014 of the first barrel 1010 is constructed so as to substantially seal the barrel 1010 leaving only the fluid communication port 1020 open. The first piston 1018 may be advanced distally, toward the distal end 1012 of the first barrel 1010 by applying a pressure to the proximal end 1040 of the first piston 1018. A second piston 1030 may be slidably disposed in the proximal end 1026 of the second barrel 1022 within the second cavity 1028. Preferably a piston rod 1034 is coupled to a distal end 1036 of the first piston 1018. The piston rod 1034 extends from the distal end 1036 of the first piston 1018 and is coupled to a proximal end 1038 of the second piston 1030. When the first piston 1018 advances, the piston rod 1034 exerts a force on the second piston 1030, causing the second piston 1030 to also advance.

The first barrel 1010 may be constructed to include a vent 1044 toward the distal end 1012 of the first barrel 1010. The vent 1044 allows excess pressure that builds up in the first cavity 1016 to be released as the first piston 1018 slides toward the distal end 1012 of the barrel 1010. This release of pressure facilitates the movement of the first piston 1018.

The actuator 1000 may be used to exert hydraulic pressure on an apparatus for delivering bone cement or other flowable materials into a vertebra or other bone structure such as that depicted in FIG. 1. Hydraulic pressure is created by delivering saline or other fluid through the fluid communication port 1020 into a proximal section of the first chamber. As a result of the hydraulic pressure, the first piston 1018 may be advanced distally to cause the piston rod 1034 and the second piston 1030 to similarly advance distally. Since the cross section of the second piston 1030 is smaller than the cross section of the first piston 1018, the pressure exerted by the second piston 1030 will be greater that the pressure exerted by the first piston 1018. The cross section of the first piston 1018 must be greater than the cross section of the second piston 1030. In one embodiment, the cross section of the first piston 1018 is at least 1.05 times larger than the cross section of the second piston 1018 and the cross section of the first piston is not more than 10.05 times larger than the cross section of the second piston 1018. In another embodiment, the cross section of the first piston 1018 is up to 100 times larger than the cross section of the second piston 1030.

This embodiment may allow bone cement to be delivered without subjecting a syringe or other delivery device to torque. Furthermore, since the syringe cross section, and the piston cross section decrease over the length of the syringe, the hydraulic pressure is multiplied, thereby allowing a lower pressure to be exerted at the proximal end 1014 of the first piston 1018 while still providing adequate pressure at the distal end 1024 of the second barrel 1022 to force the bone cement through the delivery device. For example, in the illustrated embodiment, the cross-sectional area of the first piston 1018 is approximately three times the size of the cross-sectional area of the second piston 1030. Therefore, the pressure exerted by the second piston 1030 will be nine times the pressure exerted by the first piston 1018.

While described in terms of hydraulic pressure, the apparatus may also be used with a gas or pressurized gas.

Figure 11:
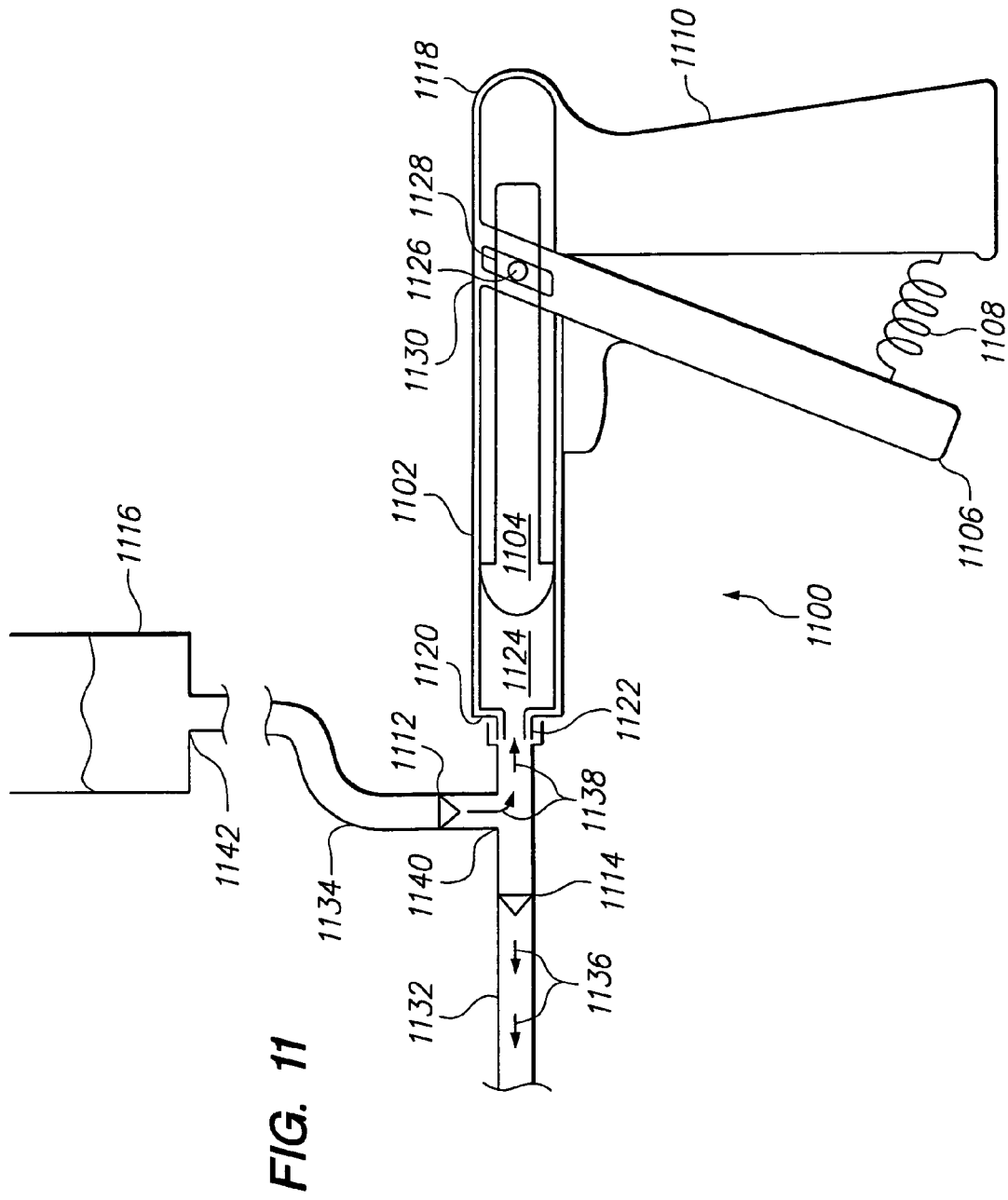
FIG. 11 is a partial cross-sectional side view of another actuator for use with the apparatus of FIG. 1.

FIG. 11 illustrates an actuator 1100 in accordance with an embodiment of the invention. The actuator 1100 is a pump that creates and delivers pressure. The actuator 1100 generally includes a barrel 1102 including a proximal end 1118, a distal end 1120, and a fluid communication port 1122 that defines a cavity 1124. Slidably disposed within the cavity 1124 is a small bore plunger 1104. The actuator 1100 further includes a trigger element 1106 having a spring 1108 connected to a handle 1110.

The small bore plunger 1104 is to coupled and controlled by the trigger element 1106. A pin 1126 slidably disposed within a channel 1128 located at a proximal end 1130 of the trigger element 1106 couples the small bore plunger 1104 to the trigger element 1106. The small-bore plunger 1104 could be coupled by other means, the pin coupling mechanism is illustrative only and not intended to be a limitation.

The fluid communication port 1120 is connected to a first tubing 1132. The first tubing 1132 may be permanently connected to the fluid communication port 1120, or alternatively, a connector 1122 may be provided to couple the first tubing 1132 to the fluid communication port 1120. The opposite end (not shown) of the first tubing 1132 is connected to an opening a proximal end of a bone cement delivery device, such as the opening 170 in the barrel 152 of the syringe 150 of FIG. 1.

Disposed within the first tubing 1132 is a first one-way valve 1114. The first one-way valve 1114 allows for fluid or gas flow in one direction only, namely in a direction distal from the valve as illustrated by flow arrows 1136.

A second tubing 1134 having a first end 1140 is connected to the first tubing 1132 at a location distal the fluid communication port 1122 and proximal the first one-way valve 1114. The second tubing 1134 may be permanently connected to the first tubing 1132. Alternately, connectors (not shown) may be used to join the first tubing 1132 and the second tubing 1134. Disposed within the second tubing 1134 is a second one-way valve 1112. The second one-way valve 1112 allows for fluid or gas flow in one direction only, namely in a direction distal from the second one-way valve 1112 as illustrated by flow arrows 1138. A second end 1142 of the second tubing 1134 is connector to a water outlet 1144 on the water reservoir 1116. The second end 1142 may be permanently connected to the water outlet 1144. Alternatively, complementary connectors (not shown), may be used to connect the second end 1142 to the water outlet 1144.

The actuator 1100 may be used to exert pressure on a piston in an apparatus for delivering bone cement or other flowable materials into a vertebra or other bone structure (not shown) so that the flowable compound is forced into the vertebra. After the actuator 1100 is connected to the first tubing 1132 and the second tubing 1134, water from the water reservoir 1116 is released into the second tubing 1134. The water flows through the second tubing 1134, through the second one-way valve 1112 and into the cavity 1124 through the fluid communication port 1122 of the barrel 1102. Once in the cavity 1124 the trigger element 1106 is depressed compressing the spring 1108 toward the handle 1110, and pressurizing the water in the chamber 1124 with the small bore plunger 1104. The trigger element 1106 is then released, allowing the spring 1108 to extend and pull the small bore plunger 1104 toward the proximal end 1118 of the barrel 1102. This pulling action pulls the water out tube 1134 in the direction of arrow 1138. The second one-way valve 1114 in the first tubing 1132 prevents the water from being pulled from the distal end to the check valve 1114. Once the water passes the first one-way valve 1112 it is prevented from flowing back into the second tube 1134. The trigger element 1106 is repeatedly depressed and released to force water into the first tubing 1132 to build-up pressure. The actuator 1100 operates by dispensing the force in an incremental manner similar to a pumping action.

The first tubing 1132, is connected to a bone cement delivery device as described above. The pressure increase in the first tubing 1132 causes the water to flow through the first tubing 1132 and into a proximal chamber of the cement delivery device, such as the proximal chamber 168 in the barrel 152 of the syringe 150 of FIG. 1. The water pressure in the proximal chamber pushes a piston, such as the piston 164 in FIG. 1 towards a distal end of the delivery device, thereby forcing the flowable compound out of the cavity and into the outlet port for delivery into the cannula.

The actuator 1100 may be equipped with a pressure relief valve, or alternately, a pressure relief valve may be provided on the first tubing 1132 distal one-way valve 1114 to allow for immediate reduction of pressure in the first tubing 1132, which facilitates ceasing the delivery of the flowable compound to the cannula.

Furthermore, while described as having an external water reservoir 1116, the actuator 1100 may be equipped with an internal water reservoir, for example, located within the handle 1110. If so equipped, tubing or a connecting channel would run from the internal water source to the distal end 1120 of the barrel 1102.

While the actuator 1100 is described with relationship to water, this is not intended to be a limitation and various fluids or gases may be equally suitable for use with the device.

Figure 12:
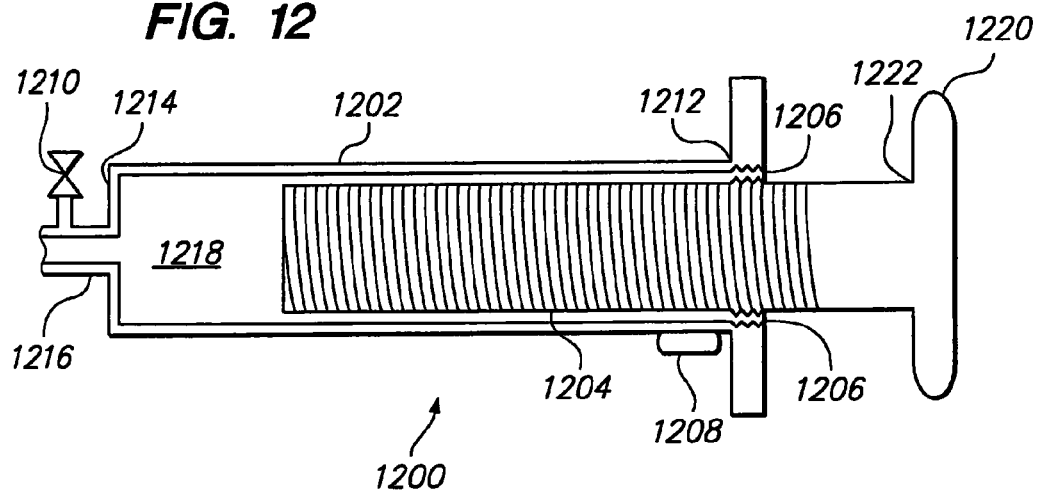
FIG. 12 is a partial cross-sectional side view of still another actuator for use with the apparatus of FIG. 1.

FIG. 12 illustrates an actuator 1200 in accordance with another embodiment of the invention. Generally, the actuator 1200 is a torque actuator that creates and delivers pressure. The actuator 1200 generally includes a barrel 1202 including a proximal end 1212, a distal end 1214, and a fluid communication port 1216 that defines a cavity 1218. Disposed within the cavity 1218 is a screw piston 1204. The screw piston 1204 is designed with a handle 1220 at a proximal end 1222. The handle 1220 allows an operator to easily rotate the screw piston 1204. The handle 1220 may be an integral part of the screw piston 1220 or may be a separate part. Optionally, the screw piston 1204 can be constructed such that the piston (not shown) is a separate component. If designed in this way, the thread of the screw piston 1204 would rotate to advance the piston, but the piston itself would not rotate but would merely advance longitudinally through the barrel 1202.

The actuator further comprises a threaded connector 1206, designed to mate with the screw piston 1204 such that rotation of the screw piston 1204 about its longitudinal axis causes the screw piston 1204 to move axially, i.e., to advance and/or retract the screw piston 1204 within the barrel 1202. The threaded connector 1206 may engaged or disengaged the screw piston 1204 by a means of piston release mechanism 1208. The screw piston 1204 may be disengaged for a number of reasons, e.g., to relieve pressure, or to reset the piston screw 1204.

Optionally, there may be a pressure release valve 1210 located on the fluid communication port 1216.

Attached to the fluid communication port 1216 is a tubing (not shown). The opposite end (also not shown) of the tubing is connected to an opening in a bone cement delivery device, such as the opening 170 in the barrel 152 of the syringe 150 of FIG. 1.

The actuator 1200 may be used to exert hydraulic pressure on a piston in an apparatus for delivering bone cement or other flowable materials into a vertebra or other bone structure (not shown). In operation, the cavity 1218 of the barrel 1202 is filled with a fluid. The tubing is attached to the fluid communication port 1216 as stated above. The tubing may be attached to the fluid communication port 1216 prior to attaching the opposite end to the opening in the bone cement delivery device, and the tubing may then used to facilitate filling the cavity 1218 with the fluid. Alternatively, the tubing may be attached after the cavity 1218 is filled with the fluid.

After the cavity 1218 is filled with the fluid, the screw piston 1204 is rotated to advance the screw piston 1204 through the barrel 1202 towards the distal end 1214. This action forces the water out the fluid communication port 1216 and into the tubing.

The tubing is connected to a bone cement delivery device as described above. The pressure build-up in the tubing causes the water to flow through the tubing and into a proximal chamber of the cement delivery device, such as the proximal chamber 168 in the barrel 152 of the syringe 150 of FIG. 1. The water pressure in the proximal chamber pushes a piston, such as the piston 164 in FIG. 1 towards a distal end of the delivery device, thereby forcing the flowable compound out of the cavity and into the outlet port for delivery into the cannula.

Figure 13:
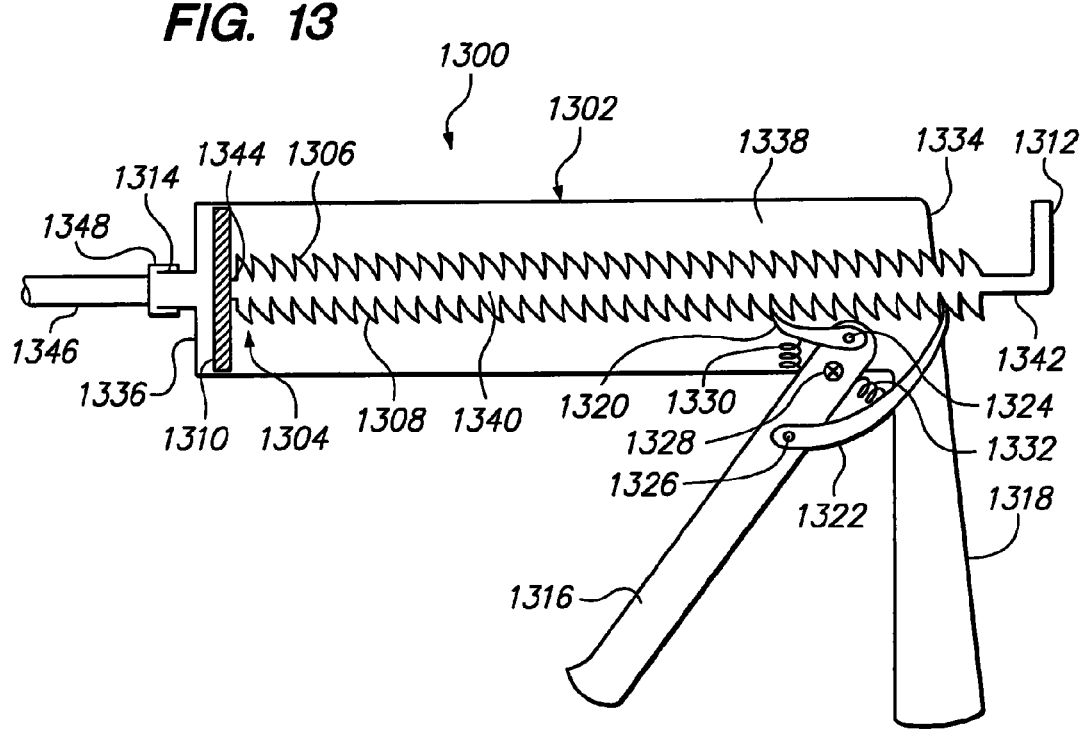
FIG. 13 is a partial cross-sectional side view of yet another actuator for use with the apparatus of FIG. 1.

While the actuator 1200 is described with relationship to water, this is not intended to be a limitation and various fluids or gases may be equally suitable for use with the device. In addition, the actuator 1200 may include a pressure gauge or other device (not shown) to monitor the delivery pressure FIG. 13 illustrates an actuator 1300 in accordance with an embodiment of the invention. The actuator 1300 creates and delivers pressure. The actuator 1300 generally includes a barrel 1302 including a proximal end 1334, a distal end 1336, and a fluid communication port 1314 that defines a cavity 1338. Slidably disposed within the cavity 1338 is a toothed driving rod 1304. The actuator 1300 further includes a trigger element 1316 having a compression spring 1330 and a tension spring 1332 connected to a top extender 1320 and a bottom extender 1322 respectively.

The toothed driving rod 1304 is coupled to and controlled by the trigger element 1316 through the top extender 1320 and the bottom extender 1322. The trigger 1316 rotates about a pivot 1328. Located on the trigger 1316 are two additional pivots, a first pivot 1324 that links the top extender 1320 to the trigger 1316 and a second pivot 1326 that links the bottom extender 1322 to the trigger 1316.

The toothed driving rod 1304 is comprised of an elongated member 1340 having a proximal end 1342 and a distal end 1344. Located at the proximal end 1342 of the toothed driving rod is a handle 1312 that may be rotated clockwise or counterclockwise. Optionally, located at the distal end 1344 of the toothed driving rod 1304 is a piston 1310. Preferably the cross-section of the piston 1310 is sized such that it is just slightly smaller than the cross section of the barrel 1302 so that the piston 1310 may slide within the barrel 1302. Along opposite sides of the axial length of the toothed driving rod 1304 are multiple protrusions, e.g., 1306, 1308. As depicted, there are two sets of protrusions: a first set of protrusions, comprised of multiple protrusions of substantially the same size and shape; and a second set of protrusions comprised of multiple protrusions of substantially the same size and shape. The first set of protrusions and the second set of protrusions are oriented in opposing directions. The first set of protrusions and the second set of protrusions lie approximately 180 degrees apart along the axial length of the elongated member 1340. The individual protrusions in each set are spaced substantially equal distance apart along the axial length. Although depicted in a particular geometry, the geometry shown is not intended to be a limitation on the design of the protrusions. The protrusions 1306, 1308 may be of any shape that is capable of engaging the top extender 1320 and the bottom extender 1322 when the actuator 1300 is in use.

A grip 1318 is located toward the proximal end of the barrel 1302 to facilitate the operation of the trigger 1316.

The fluid communication port 1314 is connected to a tube 1346. The tube 1346 may be permanently connected to the fluid communication port 1314, or alternatively, a connector 1348 may be provided to couple the tube 1346 to the fluid communication port 1314. The opposite end (not shown) of the tube 1346 is connected to an opening at the proximal end of a bone cement delivery device, such as the opening 170 in the barrel 152 of the syringe 150 of FIG. 1.

The cavity 1338 of the barrel 1302 is filled with saline or other fluid. The actuator 1300 may be delivered prefilled with saline when packaged, or may be filled just prior to use.

The actuator 1300 is used to exert pressure on a piston in an apparatus for delivering bone cement or other flowable materials into a vertebra or other bone structure (not shown) so that the flowable compound is forced into the vertebra. After the actuator 1300 is connected to the first tubing 1346 and the cavity 1338 is filled with saline, the trigger element 1316 is depressed towards the grip 1318. This action forces the top extender 1320 toward the distal end 1336 of the barrel 1302, which then forces the toothed driving rod 1304 to advance toward the distal end 1336 of the barrel 1302 by engaging one of the protrusions 1308. Alternatively, there could be more than one extrusion to engage with the toothed driving rod 1304. The trigger element 1316 is repeatedly depressed and released causing the top extender 1320 to engage with the protrusions progressing toward the proximal end 1342 of the toothed driving rod 1304. This repeated depression and release of the trigger element 1316 forces the saline from the cavity 1338 into the first tubing 1346 to build-up pressure. The actuator 1300 operates by dispensing the pressure in an incremental manner.

The tube 1346 is connected to a bone cement delivery device as described above. The pressure increase in the tube 1346 causes the saline to flow through the tube 1346 and into a proximal chamber of the cement delivery device, such as the proximal chamber 168 in the barrel 152 of the syringe 150 of FIG. 1. The fluid pressure in the proximal chamber pushes a piston, such as the piston 164 in FIG. 1 towards a distal end of the delivery device, thereby forcing the flowable compound out of the cavity and into the outlet port for delivery into the cannula.

The actuator 1300 is also configured to relieve the pressure that has been built-up in the actuator 1300 when it is used as described above. One way the pressure may be relieved is incrementally. The incremental reduction in pressure is accomplished by rotating the handle 1312 180 degrees about its longitudinal axis. The trigger element 1316 is then depressed toward the grip 1318. The trigger element 1316 forces the bottom extender 1322 towards the proximal end 1334 of the barrel 1302, which then forces the toothed driving rod 1304 to advance toward the proximal end 1334 of the barrel 1302 by engaging one of the protrusions 1306 in the opposing direction. Therefore, the toothed driving rod 1304 moves incrementally toward the proximal end 1334 of the barrel 1302.

Alternatively, the pressure built up in the actuator 1300, when in operation, may be relieved by simply disengaging the protrusions 1308, from the top extender 1320. The barrel 1302 could be configured with a push button (not shown) that would cause the tension spring 1330 and the compression spring 1332 to constrict. Once constricted, the top extender 1320 and the bottom extender 1322 would no longer be in contact with the protrusions 1308, 1306, and the toothed drive rod 1304 could be pulled toward the proximal end without being restricted by the protrusions 1306, 1308.

In another embodiment of the actuator 1300, a secondary barrel (not shown) is disposed within the barrel 1302. The secondary barrel is filled with saline or other fluid as described previously. The secondary barrel may be delivered prefilled with saline when packaged, or may be filled just prior to use. The secondary barrel has a distal end and a proximal end. At the distal end, there is an outlet. The outlet is connectable to the tube 1346, either directly or through the fluid communication port 1314 on the distal end 1336 of the barrel 1304. A piston is slideably disposed within an interior cavity of the secondary barrel. The toothed driving rod 1304 is linked to the piston in the secondary barrel such that a proximal or distal motion in the toothed driving rod produces the same motion in the piston in the secondary barrel. Operating the actuator for pressure exertion as described above, the toothed driving rod 1304 exerts a proximally oriented force on the piston in the secondary barrel forcing the piston toward the distal end of the secondary barrel 1336. This results in forcing the fluid out of the secondary barrel. Operating the actuator for pressure relief as described above, the toothed driving rod 1304 exerts a distally oriented force on the piston in the secondary barrel, forcing the piston toward the proximal end of the barrel 1334.

Figure 14:
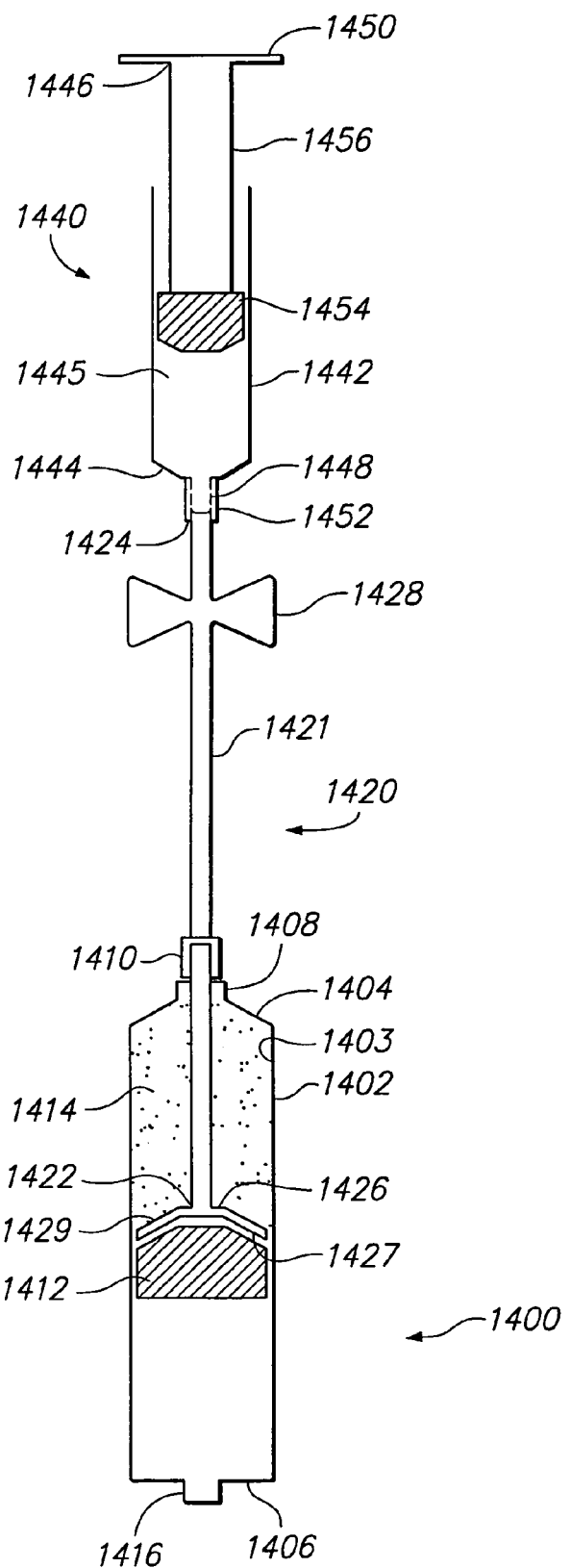
FIG. 14 is a partial cross-sectional side view of liquid delivery device for use with a mix and deliver device in accordance with an embodiment of the invention.

FIG. 14 illustrates an apparatus for introducing a liquid component from a syringe into a powder component, and specifically for mixing a two part, i.e., powder and fluid, bone cement. Generally, the apparatus includes an introducer syringe 1440, a mix and delivery syringe, or mixing unit 1400, and a mixing rod 1420.

The introducer syringe 1440 generally includes a barrel 1442 including a proximal end 1446, and a distal end 1444, thereby defining an interior space or cavity 1445 within which a liquid component, such as monomer, may be stored. The distal end 1444 includes an outlet port 1448 that is in fluid communication with the cavity 1445. A luer lock or other connector 1452 may be provided on the outlet port 1448 for connecting to a proximal end 1424 of the mixing rod 1420. The mixing rod 1420 may alternatively be configured with a complimentary connector (not shown) for joining with the connector 1452 on the outlet port 1448.

The mixing rod 1420 generally includes a shaft 1421 having a proximal end 1424, and a distal end 1422. The shaft 1421 is hollow with an axial lumen extending from the proximal end 1424 to the distal end 1422. Located near the proximal end 1424 of the shaft 1421 is a handle 1428. At the distal end 1422 of the shaft 1421 is a mixing element 1426. The mixing element 1426 preferably has multiple openings to facilitate mixing and is sized such that the mixing element 1426 contacts or is in close proximity to an interior surface 1403 of a barrel 1402 of a mix and delivery unit 1400 while still being able to slide within the barrel 1402. Preferably, the mixing element 1426 is shaped so that the distal surface 1427 of the mixing element 1426 is substantially flush with a piston 1412 disposed within a cavity 1414 of the mix and delivery syringe 1400 when the mixing element 1426 abuts the piston 1412. A proximal surface 1429 of the mixing element 1426 is shaped so that the proximal surface 1429 is substantially flush with the distal end 1404 of the barrel 1402 when the mixing element 1426 abuts the distal end 1404 of the barrel 1402. It is desirable to have the mixing element 1426 shaped in this manner to ensure thorough mixing and that no powder remains unmixed in any portion of the barrel 1402.

The mix and delivery syringe generally includes a barrel 1402 including a proximal end 1406, and a distal end 1404, thereby defining an interior space or cavity 1414 within which a powder component (not numbered), such as a bone cement powder, may be stored. The proximal end 1406 includes an opening 1416 that is connectable to an actuating device. The distal end 1404 includes an inlet port 1408 that is in fluid communication with the cavity 1414. A seal 1410, such as a rotary seal, may be provided on the inlet port 1408. A piston 1412 may be slidably disposed within the cavity 1414; the piston 1412 may be used to force the multi-component compound within the cavity 1414 out through the inlet port 1408 after the compound is mixed.

In use, the mixing rod 1420 is inserted within the barrel 1402 of the mix and delivery syringe 1400. The introducer syringe 1440 filled with a liquid component, e.g., a monomer, is connected to the proximal end 1424 of the shaft 1421 of the mixing rod 1420. The introducer syringe 1440 is connected in a manner that allows the liquid component in the syringe to be inserted through the shaft 1421 and into the cavity 1414 of the mix and deliver syringe 1400. The circumference of the shaft 1421 of the mixing rod 1420 is sealed with a rotary seal 1410 at the inlet port 1408 of the mix and delivery syringe 1400. Pressing down against the piston 1412 with the mixing element 1426 on the distal end 1422 of the mixing rod 1420 retracts the piston 1412 within the cavity 1414 of the mix and delivery syringe 1400. The mixing element 1426 may be forced downward on the piston 1412 by placing a downward force on the handle 1428 of the mixing rod 1420. Causing the piston 1412 to retract causing a low-pressure area inside the bone cement reservoir. This pressure differential causes the liquid to be drawn in to the mix and delivery syringe 1400 so that the liquid may be combined with the powder component, e.g., bone cement powder. Since there is not positive pressure in the mix and delivery device 1400, the liquid is introduced without leakage or a need to vent air from the device.

The powder component may be prepacked in the mix and deliver syringe 1400 or may be added to the syringe prior to inserting the mixing rod 1420. Similarly, the introducer syringe may be prepacked with the liquid or the liquid may be drawn into the syringe using conventional means.

As noted previously, the forgoing descriptions of the specific embodiments are presented for purposes of illustration and description. They are not intended to be exhaustive or to limit the invention to the precise forms disclosed and obviously, many modifications and variations are possible in view of the above teachings. The embodiments were chosen and described in order to explain the principles of the invention and its practical applications, to thereby enable those skilled in the art to best utilize the invention and various embodiments thereof as suited to the particular use contemplated. It is intended that the scope of the invention be defined by the following claims and their equivalents.

What is claimed:

1. An apparatus for mixing and dispensing a multi-component bone cement into a vertebrae, comprising:
    a cannula, sized for insertion into a vertebrae, comprising a proximal end, and a distal end, wherein both the distal end and the proximal end are open and a lumen extends therethrough;
    a mix and deliver device comprising a barrel having a distal end and a proximal end thereby defining a cavity for mixing a flowable compound therein, wherein the distal end further comprises an outlet in fluid communication with the cavity;
    a hollow pivot connector configured to link the mix and deliver device to the cannula, wherein the pivot connector comprises a first and a second segment and wherein the first and second segments allow the pivot connector to rotate about two non-collinear axes which are oriented at an angle from each other, each of said first and second segments having a sealing mechanism providing a fluid tight seal within the pivot connector at fluid pressures of 1000 psi to 3000 psi; and
    a mixing rod having an elongate shaft, said elongate shaft having a lumen therethrough with open ends and a plurality of ports in fluid communication with said lumen spaced along the axial length of the shaft, a handle disposed on a proximal end of the elongate shaft and a mixing element disposed on a distal end of the elongate shaft, the mixing rod slidably disposed within said cavity of said mix and deliver device such that said proximal end of said elongate shaft extends through said outlet and said mixing element is contained within said cavity.

2. The apparatus of claim 1, wherein the flowable compound comprises a bone cement.

3. The apparatus of claim 1, further comprising a piston slidably disposed within the cavity of the barrel, the piston configured to deliver the flowable compound through the outlet to the cannula.

4. The apparatus of claim 3, wherein the barrel further comprises an opening at the proximal end and wherein an actuating device for applying a fluid pressure is connected to the opening, the fluid pressure causing the piston to axially advance within the barrel.

5. The apparatus of claim 4, further comprising a tube wherein the tube comprises a distal end coupled to the opening and a proximal end coupled to the actuating device.

6. The apparatus of claim 4, wherein the piston divides the cavity into a distal area for mixing and storing a flowable compound and a proximal area, wherein the proximal area is designed to receive the pressure from the actuating device.

7. The apparatus of claim 1, further comprising a stand connectable to the mix and deliver device wherein the stand supports the mix and deliver device at an angle relative to a body.

8. The stand of claim 7, wherein the stand is integral to the mix and deliver device.

9. The apparatus of claim 1, further comprising a removable connector located on the outlet, the removable connector configured to ensure the outlet is clear prior to connecting the mix and deliver device to the cannula.

10. The apparatus of claim 1, further comprising a removable connector located on the outlet, the removable connector configured to ensure the outlet is clear prior to connecting the mix and deliver device to the hollow pivot connector.

11. An apparatus for mixing and dispensing a flowable compound, comprising:
    a mix and deliver device comprising a barrel having a distal end and a proximal end thereby defining a cavity within which a flowable compound may be mixed, the distal end comprising an outlet in fluid communication with the cavity, an inlet port located on the circumference of the barrel which is in fluid communication with the cavity, and a piston slidably disposed within the cavity of the barrel; and
    a mixing rod having hollow elongate shaft, said elongate shaft comprising a cylindrical wall with open ends having a lumen extending axially therethrough in communication with said open ends, said cylindrical wall having a plurality of fluid access ports therein spaced along the axial length of the shaft, said fluid access ports in fluid communication with said lumen so as to allow fluids that have been inserted into the lumen of the hollow shaft to exit the lumen at various locations along the hollow shaft, a handle disposed on a proximal end of the elongate shaft and a mixing element disposed on a distal end of the elongate shaft, the mixing rod slidably disposed within said cavity of said mix and deliver device such that said proximal end of said elongate shaft extends through said outlet and said mixing element is contained within said cavity.

12. The apparatus of claim 11, wherein the mixing rod is slidably disposed within the cavity through the outlet.

13. The mix and deliver device of claim 11, wherein the inlet port is located nearer the proximal end of the cavity.

14. The mix and deliver device of claim 11, wherein the fluid access ports are also spaced around the circumference of the hollow shaft.

15. An apparatus for introducing a liquid, comprising:
    an introducer comprising a proximal end and a distal end defining an introducer cavity within which a liquid may be contained, the introducer having an outlet and a piston slidable within said introducer cavity for forcing liquid from said introducer cavity out through the outlet;
    a mix and delivery device comprising a proximal end and a distal end defining a delivery cavity within which a slideable piston is disposed and wherein the distal end further comprises an inlet port;
    a mixing rod configured to provide fluid communication between the introducer and the mix and delivery device comprising, a shaft having a proximal end and a distal end wherein the proximal end and the distal end are open and wherein a lumen extends therethrough, the proximal end of said shaft in fluid communication with said outlet of said introducer, and the distal end of said shaft disposed within said delivery cavity.

16. The apparatus of claim 15, wherein a seal is disposed about the periphery of the inlet port.

17. The apparatus of claim 16, wherein the seal is a rotary seal.

18. The apparatus of claim 16, further comprising a mixing element disposed at the distal end of the shaft and a handle disposed near the proximal end of the shaft.

19. The apparatus of claim 18, wherein a distal surface of the mixing element is substantially flush with a proximal surface of the piston.

20. The apparatus of claim 18, wherein the piston may be displaced by exerting a force on the handle.

21. The apparatus of claim 15, wherein the piston may be displaced by exerting a force on the mixing rod.

\* \* \* \* \*